United States Patent [19]
Arnold, Jr. et al.

[11] Patent Number: 5,792,615
[45] Date of Patent: Aug. 11, 1998

[54] SYNTHETIC OLIGOMERS HAVING CHIRALLY PURE PHOSHONATE INTERNUCLEOSIDYL LINKAGES MIXED WITH NON-PHOSPHONATE INTERNUCLEOSIDYL LINKAGES

[75] Inventors: Lyle J. Arnold, Jr., Poway; Richard I. Hogrefe; Mark A. Reynolds, both of San Diego; Timothy A. Riley, Nipomo; David A. Schwartz, Encinitas, all of Calif.

[73] Assignee: Genta, Incorporated, San Diego, Calif.

[21] Appl. No.: 812,861

[22] Filed: Mar. 6, 1997

Related U.S. Application Data

[63] Continuation of Ser. No. 154,014, Nov. 16, 1993, abandoned.

[51] Int. Cl.$^6$ .................................................. C12Q 1/68
[52] U.S. Cl. ........................... 435/6; 536/24.5; 536/25.3
[58] Field of Search ..................... 455/6; 536/24.5, 536/25.3, 25.33, 26.7, 26.8

[56] References Cited

U.S. PATENT DOCUMENTS 5,212,295   5/1993   Cook .................................... 536/26.7

FOREIGN PATENT DOCUMENTS

92/02532   2/1992   WIPO.

OTHER PUBLICATIONS

Neckers et al., Critical Rev. Oncogenesis, 3(1,2):175–231, 1992.

*Primary Examiner*—Scott W. Houtteman
*Attorney, Agent, or Firm*—Knobbe, Martens, Olson and Bear, LLP

[57] ABSTRACT

Oligomers having chirally pure phosphonate internucleosidyl linkages mixed with non-phosphonate internucleosidyl linkages which hybridize to RNA target sequences and methods for their preparation are provided.

20 Claims, No Drawings

SYNTHETIC OLIGOMERS HAVING CHIRALLY PURE PHOSHONATE INTERNUCLEOSIDYL LINKAGES MIXED WITH NON-PHOSPHONATE INTERNUCLEOSIDYL LINKAGES

This application is a continuation of application Ser. No. 08/154.014. filed Nov. 16. 1993 now abandoned.

BACKGROUND AND INTRODUCTION OF THE INVENTION

The present invention is directed to synthetic oligomers having chirally pure phosphonate internucleosidyl linkages mixed with non-phosphonate internucleosidyl linkages and to methods for their synthesis.

Oligomers having naturally occurring phosphodiester internucleosidyl linkages and certain other internucleosidyl linkages do not have chiral centers at the phosphorus atom (or other atom) of the internucleosidyl linkage.

However, these phosphonate internucleosidyl linkages which include methylphosphonate and methyl phosphonothioate internucleosidyl linkages are chiral at depending on the relative orientation of the alkyl group. Thus, Oligomers having such linkages may theoretically have $2^n$ different diastereomeric forms for a particular Oligomer where n is the number of chiral internucleosidyl linkages in the Oligomer sequence. For example, a 21-mer having 10 chiral internucleosidyl linkages and 10 non-chiral linkages theoretically would have 1,024 diastereoisomers and a 37-mer having 18 chiral internucleosidyl linkages theoretically would have 262,144 diastereoisomers.

The reported effects of chirality of internucleosidyl linkages on the resulting Oligomers and their biological or physical chemical behavior have been varied.

The preparation of two isomers of decathymidylate analogues having stereoregular, alternating methyl-phosphonate and phosphodiester backbones has been reported (Miller, et al., J. Biol. Chem. 255(20):9659–9665 (1980). Complexes between the two isomers and complementary polynucleotides were studied. The absolute configurations of the methylphosphonate groups of isomers 1 and 2 were not determined. Complexes formed by the two isomers with complementary polynucleotides were said to have different stoichiometries and thermal stabilities. Miller et al. hypothesized that in formation of a complex with a decathymidylate analog whose methylphosphonate groups were in the S-configuration the methyl group should have the least perturbational effect on solvent interactions with the complex; whereas, in contrast, complex formation with the decathymidylate analog whose methylphosphonate groups have the R-configuration would orientate the methyl group away from the base stacking region and toward the solvent and should result in "unfavorable interactions between the exposed methyl groups and the surrounding solvent."

Studies on complexes of duplex formation between a 19-mer phosphodiester oligonucleotide ($dA_{19}$, $dU_{19}$ or $dT_{19}$) and a 19-mer methylphosphonate oligonucleotide having one phosphodiester 5'-internucleosidyl linkage ($dA^*_{19}$, $dU^*_{19}$ or $dT^*_{19}$) reported that transition curves for complexes between $da^*_{19}$ and $dT_{19}$ or $dU_{19}$ were sharp and similar to those for $dA_{19}$ and $dT_{19}$ or $dU_{19}$. whereas transition curves for duplexes of $dT^*_{19}$ or $dU^*_{19}$ and $dA_{19}$ were significantly broader, suggesting to the authors that methylphosphonate chirality had a significant influence on binding stability only when the pyrimidine strand was substituted. (Kibler-Herzog, Laura, et al., Nucleic Acids Research 18(12):3545–3555 (1990)

A study of 2-diastereoisomeric pairs of octathymidine methylphosphonates (all Sp and SpSpSpRpSpSpSp versus all Rp and RpRpRpSpRpRpRp) compared with octathymidylic acid and a random mixture of octathymidine methylphosphonate diastereoisomers and complexes formed with penta-decadeoxyriboadenylic acid reported that configuration of the internucleosidyl methylphosphonate linkages may affect binding of $(dA)_{15}$ to the Oligomer and that the methyl in the Sp configuration decreased duplex stability. (Lesnikowski et al., Nucleic Acids Research 18(8):2109–2115 (1990).

Certain computer modeling studies reported that methylphosphonate ("MP") hybridization to a DNA target was more stable with R-MP substitution due to favorable hydrophobic interactions whereas S-MP destabilized the double helix with less favorable hydrophobic interactions. The simulations compared antisense Oligomers having a single R-MP to S-MP substitution. (Hausheer et al., J. Am. Chem. Soc. 114:3201–3206 (1992)).

Computer modeling studies to determine the relative stability of R and S methylphosphonate oligomers by free-energy perturbation approaches using a free-energy decomposition method were reported. The study reported that in the case of the S diastereomer the C2' and C3' sugar (5' direction) carbons and hydrogens unfavorably interacted with the methyl group, while the C5' sugar (3' direction) hydrogens destabilized the R diastereoisomer. Although the study reported the stability of the R-configuration to be favored, it was noted that under certain circumstances there may be reversals in stability of R and S diastereoisomers. (Ferguson and Kollman, Antisense Research and Development, 1:243–25 (1991)).

Studies of formation of duplexes using self-complementary DNA Oligomers having one methylphosphonate internucleosidyl linkage were reported. With the Rp duplexes, reported Tm increased when the substitution was closer to the 3'-end of the strand. With the Sp duplexes, substitution nearer the center of the strand was said to produce larger effects (greater Tm depressions) than substitution closer the either end of the duplex. In one instance of substitution between the second and third nucleosides (from the 5'-end), the Sp duplex had a higher Tm than the corresponding Rp duplex. (Bower et al., Nucleic Acids Research 15(12):4915–4930 (1987)).

In a summary of molecular modeling studies on single stranded, as well as base paired, forms of dinucleoside methylphosphonates it was reported that neither S-MP nor R-MP seemed to significantly alter the stereochemistry of duplex structure (Latha et al., J. Biomolecular Structure Dynamics, 9(3):613–631 (1991).

In a review article summarizing certain work on antisense agents, disadvantages of poorly hybridizing racemic oligodeoxynucleoside methylphosphonates in cell free extracts were said to be more or less balanced by their proposed advantages in cell culture systems. It was noted that certain reports using a normal (deoxyribonucleoside) octamer with one methylphosphonate linkage found the Oligomer with an R bond to have a melting temperature higher than the Oligomer with an S bond. It was also noted that sequence dependence of methylphosphonate base pairing might be as important as chirality. (Wickstrom, "Antisense DNA Therapeutics Neutral Analogs and Their Stereo-chemistry" in *Gene Regulation*: Biology of Antisense RNA and DNA, 119 to 132 (Erickson and Izant, eds., Raven Press Ltd., New York (1992))

Greater longevity, more efficient cellular uptake and lack of charge.

Diastereoselective synthesis of dinucleoside methylphosphonates containing thymidine has been reported (Engels et al., Nucleosides & Nucleotides 10(1-3):347-350 (1991)). Diastereoselective synthesis of certain other dinucleoside methylphosphonates using methyldichlorophosphine has been reported (Löschiner et al, Tetrahedron Letters 30(41):5587-5590 (1989)).

SUMMARY OF THE INVENTION

According to one aspect, the present invention provides synthetic Oligomers having mixed internucleosidyl linkages, that is oligomers having chirally pure phosphonate internucleosidyl linkages interspersed with single non-phosphonate internucleosidyl linkages and methods for their preparation. Such phosphonate internucleosidyl linkages include lower alkylphosphonate internucleosidyl linkages of 1 to 3 carbon atoms and lower alkylphosphonothioate internucleosidyl linkages of 1 to 3 carbon atoms. These mixed oligomers have phosphonate internucleosidyl linkages interspersed between single non-phosphonate internucleosidyl linkages in a ratio of from 1 to about 1 to 1 to about 4 non-phosphonate linkages to phosphonate linkages. These oligomers may be used to prevent or interfere with expression or translation of a single-stranded RNA target sequence and have a nucleoside base sequence which is sufficiently complementary to the RNA target sequence to hybridize therewith. According to a preferred aspect, such Oligomers have alternating chirally pure phosphonate internucleosidyl linkages which alternate with non-phosphonate internucleosidyl linkages.

Among other factors, the present invention is based on our unexpected finding that the mixed Oligomers described herein which have mixed internucleosidyl linkages which comprise a mixture of methylphosphonate internucleosidyl linkages that are enriched in either Rp or Sp chirality with non-phosphonate linkages display higher or lower (respectively) "net" binding affinities for their complementary RNA target sequences as compared to Oligomers of the same nucleoside base sequence having racemic methylphosphonate internucleosidyl linkages. These oligomers also exhibit increased nuclease resistance as compared with oligomers having diester, phosphonothioate or other nuclease sensitive linkages. By "net" is meant the mean of the individual binding affinities for each diastereomer in an Oligomer sample. We have found that oligomer samples that are enriched for higher binding diastereomers (that is which are enriched for Rp-configuration methylphosphonate internucleosidyl linkages) show a higher "net" binding affinity. As evidence of such binding affinities, we have demonstrated that Oligomers enriched for Rp-configurations at MP chiral centers demonstrate higher Tm's in hybridization assays with RNA target sequences than do Oligomers having racemic MP linkages and whereas Oligomers enriched for Sp configurations at MP chiral centers demonstrate lower Tm's. We have found that certain Rp enriched Oligomers demonstrate enhanced binding affinities for RNA target sequences when binding to a RNA target in a duplex. With respect to binding in a duplex mode, we have found Rp enrichment of methylphosphonate internucleosidyl linkages to give an increase in Tm of about 0.9° to 1.5° C. per internucleosidyl linkage that is in the Rp configuration as compared to a racemic configuration. According to an especially preferred aspect, we have found that Oligomers of the present invention having nucleosides with 2'-O-methylribosyl groups as sugar moieties exhibit enhanced stability to nucleases and also exhibit increased Tm's as compared to oligomers having the same internucleosidyl linkages but with 2'-deoxyribosyl sugar moieties. In particular, we have found an increase in Tm of about 1° C. per replacement of 2'-deoxyribosyl with 2'-O-methylribosyl.

Reference has previously been made to the effect of chirality on the ability of methylphosphonate oligomers to hybridize to DNA targets. There are some reports in the literature that Rp-enriched oligo-dT methylphosphonates bind more tightly to DNA than their racemic counterparts. DNA targets were used in these studies rather than RNA. In view of the structural differences between helices formed using DNA and RNA targets, such data obtained with DNA targets would not suggest an application to RNA targets. Certain important physical chemical differences between DNA and RNA are discussed below and support this point.

It is generally reported that DNA oligomers hybridized to either DNA or RNA targets adopt different helical geometries, termed B-form and A-form, respectively. These two different types of helices have dramatically different three dimensional shapes.

Differences between the A- and B-helix forms may be summarized as follows: "An A-form duplex is generally agreed to contain sugars with a C3'-endo (N-type) pucker, in which the base pairs are inclined (tilted) approximately 19° from the helix axis and swung out from the helical axis toward the edge of the helix. As a consequence, there is greater base-base overlap in A-form structures than in B-form duplexes. In B-form duplexes of DNA, the deoxyribose sugars generally adopt a C2'-endo pucker, but with a great deal of conformational flexibility. In B-form helices, the base pairs are perpendicular to the helix axis, and are centered down the middle of the helix. There are~11-12 base pairs per turn in an A-form duplex, and 10.4 base pairs for a B-form duplex." Hall, K. B., "NMR Spectroscopy of DNA/RNA Hybrids", Current Opinion in Structural Biology 3:336-339 (1993).

Since it is known, then, that hybrids formed with DNA and RNA targets can have dramatically different geometries, one would not expect that data obtained with DNA targets would be directly applicable to RNA targets. In fact a literature report using 2'-O-methyl RNA oligomers hybridized to DNA and RNA targets supports this point (S. M. Freier et al., "Gene Regulation of Antisense RNA and DNA", pp. 95–107, edited by R. P. Erickson and J. G. Izant, Raven Press, Ltd. New York, copyright 1992). Against DNA targets, both destabilization and stabilization were observed with the 2'-O-methyl modification to the sugar portion of the nucleosides, depending on the base sequence because some DNA sequences favor the A-form more than others whereas, stabilization was always observed against RNA targets. Moreover, we have observed dramatic differences in Tm with racemic methylphosphonate oligomers hybridized to DNA and RNA targets. This suggests that evaluations of oligomers with DNA targets may give misleading results when they are intended for use as antisense inhibitors of mRNA translation.

Thus, according to one aspect, antisense Oligomers having enhanced potency as antisense inhibitors of gene expression are provided which comprise Oligomers having methylphosphonate internucleosidyl linkages enhanced for the Rp configuration which are interspersed between non-phosphonate internucleosidyl linkages, preferably phosphodiester linkages. We have found that these chirally enriched MP Oligomers hybridize more tightly to RNA target sequences and also show enhanced potency inhibiting translation of RNA targets as compared with Oligomers having racemic MP internucleosidyl linkages mixed with the same non-phosphonate internucleosidyl linkages.

In an alternate aspect, the present invention is directed to a synthetic Oligomer having activity in preventing or interfering with expression of a single stranded RNA target sequence which is a Oligomer having phosphonate internucleosidyl linkages selected from the group consisting of lower alkylphosphonate internucleosidyl linkages of 1 to 3 carbon atoms and lower alkylphosphonothioate linkages of 1 to 3 carbon atoms which are mixed with non-phosphonate internucleosidyl linkages. These mixed oligomers have chirally pure phosphonate internucleosidyl linkages interspersed between single non-phosphonate internucleosidyl linkages and have a nucleoside base sequence which is complementary to the RNA target sequence. The mixed oligomers have a ratio of non-phosphonate to phosphonate internucleosidyl linkages of from 1 to about 1 to 1 to about 4 non-phosphonate to phosphonate linkages. Preferred chirally pure phosphonate linkages include Rp lower alkylphosphonate linkages, more preferred are Rp methylphosphonate internucleosidyl linkages. Preferred non-phosphonate linkages include phosphodiester, phosphorothioate, phosphorodithioate, phosphoramidite, phosphorofluoridate, boranophosphate, formacetal and silyl internucleosidyl linkages. According to an especially preferred aspect, Rp-enriched Oligomers are provided having chirally pure Rp-methyl phosphonate linkages which alternate with phosphodiester linkages. These alternating oligomers have been found to exhibit enhanced binding affinity for an RNA target sequence.

According to an alternate preferred aspect, the nucleosides of these mixed oligomers have 2'-O-methylribosyl groups as sugar moieties. We have found mixed oligomers having 2'-O-methyl nucleosides and chirally pure Rp methylphosphonate linkages alternating with phosphodiester linkages to exhibit further enhancement of binding affinity to an RNA target sequence. We have also found that incorporation of 2'-O-methyl nucleosides in these mixed oligomers enhances stability of the oligomer to certain nucleases in comparison to oligomers having 2'-deoxynucleosides.

According to a further aspect, the present invention provides a synthetic oligomer preparation consisting of oligomers having chirally pure phosphonate internucleosidyl linkages selected from the group consisting of lower alkylphosphonate linkages of 1 to 3 carbon atoms and lower alkylphosphonothioates of 1 to 3 carbon atoms mixed with non-phosphonate linkages wherein the phosphonate linkages are interspersed between single non-phosphonate linkages and the oligomers are complementary to an RNA target sequence and wherein these oligomer preparations demonstrate enhanced "net" binding affinity for the RNA target sequence.

In another aspect, the present invention provides methods of preparing oligomers having a predetermined base sequence of nucleosidyl units and having chirally pure phosphonate internucleosidyl linkages mixed with non-phosphonate linkages wherein the phosphonate linkages are interspersed between single non-phosphonate linkages, which methods comprise coupling to each other individual nucleoside dimers, trimers or tetramers of preselected nucleoside base sequence having chirally pure phosphonate internucleosidyl linkages.

According to a further aspect, provided are novel chirally pure synthons of the formula:

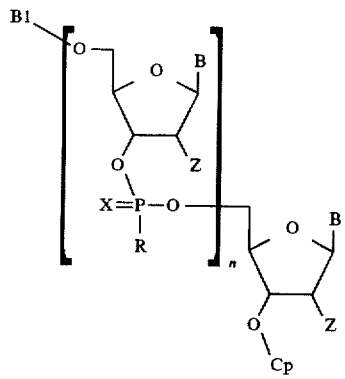

wherein X is oxygen or sulfur, R is lower alkyl of 1 to 3 carbon atoms, B1 is a blocking group removable under non-adverse conditions, Z is hydrogen, alkoxy of 1 to 10 carbon atoms, halogen or alkenyloxy of 3 to 6 carbon atoms; B is an optionally protected purine or pyrimidine base; n is 1, 2 or 3 and Cp is a coupling group. The coupling group Cp is conveniently selected so as to give the desired non-phosphonate internucleosidyl linkage when coupled to another synthon.

In an especially preferred aspect, the present invention provides methods of preparing a synthetic Oligomer which exhibits enhanced binding to an RNA target sequence. In one embodiment, this method includes the steps of identifying a single stranded target sequence and synthesizing a Oligomer having Rp-configuration methylphosphonate internucleosidyl linkages mixed with non-phosphonate linkages, more preferably phosphodiester linkages wherein the Oligomer is complementary to the identified RNA target sequence. oligomers having Rp-MP linkages alternating with phosphodiester linkages exhibit enhanced binding to a RNA target sequence in comparison to an Oligomer complementary to the RNA target sequence having random racemic methylphosphonate alternating with phosphodiester internucleosidyl linkages. According to a particularly preferred aspect, synthetic Oligomers of the present invention may be synthesized by linking together nucleoside dimers, trimers or tetramers having chirally pure Rp-configuration methylphosphonate internucleosidyl linkages.

In a further aspect, the present invention provides methods for preparing an Oligomer having a predetermined base sequence of nucleoside units and which has chirally pure phosphonate internucleosidyl linkages mixed with non-phosphonate internucleosidyl linkages which comprises linking together individually selected synthons having chirally pure phosphonate internucleosidyl linkages which synthons have the formula:

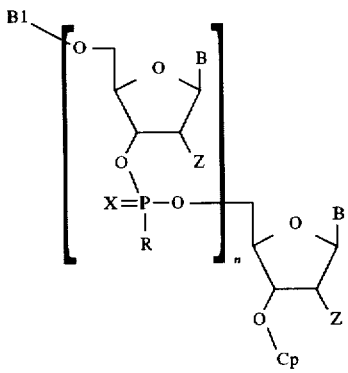

wherein X is oxygen or sulfur, R is lower alkyl of 1 to 3 carbon atoms, B is an optionally protected purine or pyrimidine base, B1 is a blocking group, Z is hydrogen, alkoxy of 1 to 10 carbon atoms, halogen or alkenyl of 3 to 6 carbon atoms; n is 1, 2 or 3; and Cp is a coupling group selected so as to give the desired non-phosphonate internucleosidyl linkages when coupled to another nucleoside.

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-analogs such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "phosphonate" refers to the group

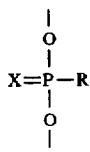

wherein X is oxygen or sulfur, R is hydrogen or an alkyl or aryl group, and thus includes various example of phosphonate and phosphonothioate internucleosidyl linkages. Suitable alkyl or aryl groups include those which do not sterically hinder the phosphonate linkage or interact with each other. The phosphonate group may exist in either an "R" or an "S" configuration. Phosphonate groups may be used as internucleosidyl linkages (or links) to connect nucleosidyl unit or a nucleosidyl unit and a non-nucleosidy monomeric unit.

The term "lower alkylphosphonate" refers to groups where X is oxygen and R is lower alkyl of 1 to 3 carbon atoms. "Methylphosphonate" refers to groups where X is oxygen and R is methyl. The term "phosphonothioate" refers to those groups where X is sulfur. The term "lower alkylphosphonothioate" refers to groups where X is sulfur and R is lower alkyl of 1 to 3 carbon atoms. The term "methylphosphonothioate" refers to a phosphonothioate group wherein R is methyl.

The term "phosphodiester" or "diester" refers to

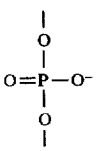

wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and arylphosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl- phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside or nucleoside/non-nucleoside polymer that the Oligomer conjugate comprises be substantially neutral.

The term "substantially neutral" in referring to an Oligomer refers to those Oligomers in which at least about 80 percent of the internucleosidyl linkages between the nucleoside monomers are nonionic linkages.

The term "acid resistant" refers to Oligomers which are resistant, in comparison to deoxyribooligo-nucleotides, to acid-catalyzed depurination by hydrolysis of the N-glycosyl bond.

The term "Triplex Oligomer Pair" refers to first and second Oligomers which are optionally covalently linked at one or more sites and which are complementary to and are capable of hydrogen bonding to a segment of a single stranded target nucleic acid, such as RNA or DNA, and, thus, together with the single stranded target nucleic acid, are capable of forming a triple helix structure therewith.

The term "Third Strand Oligomer" refers to Oligomers which are capable of hybridizing to a segment of a double stranded nucleic acid, such as a DNA duplex, an RNA duplex or a DNA-RNA duplex, and forming a triple helix structure therewith.

The term "complementary," when referring to a Triplex Oligomer Pair (or first and second Oligomers) or to a Third Strand Oligomer, refers to Oligomers having base sequences which are capable of forming or recognizing hydrogen bonds (and base pairing or hybridizing) with the base sequence of the nucleic acid to form a triple helix structure.

The term "substantially complementary" refers to Oligomers, including Triplex Oligomer Pairs or Third Strand Oligomers which may lack a complement for each nucleoside in the target sequence, have sufficient binding affinity for the target sequence to form a stable duplex or triple helix complex, as the case may be, and thereby specifically recognize the target sequence and selectively inhibit or down-regulate its expression.

The term "triplet" or "triad" refers a hydrogen bonded complex of the bases of three nucleosides between a base (if single stranded) or bases (if double stranded) of a target sequence, a base of a Second Strand and a Third Strand (if a single stranded target sequence) or a base of a Third Strand (if a double-stranded target).

"MP(Rp)" refers to a methylphosphonate internucleosidyl linkage of Rp chirality.

"MP(PS)" refers to a methylphosphonothioate internucleosidyl linkage.

"MP(Rp)(PS)" refers to a methylphosphonothioate internucleosidyl linkage of Rp chirality.

An oligomer having "alternating MP(Rp)/DE internucleosidyl linkages" refers to an Oligomer wherein methylphosphonate linkages of Rp chirality alternate with phosphodiester linkages ("DE").

An oligomer having "alternating MP(Rp)/PS internucleosidyl linkages" refers to an oligomer wherein methylphosphonate linkages of Rp chirality alternate with phosphorothioate linkages ("PS").

An oligomer having "alternating MP(Rp)(PS)/DE internucleosidyl linkages refers to an oligomer wherein methylphosphonothioate linkages of Rp chirality alternate with phosphodiester linkages.

An oligomer having "alternating MP(Rp)(PS)/PS internucleosidyl linkages" refers to an oligomer wherein methylphosphonothioate linkages of Rp chirality alternate with phosphorothioate linkages.

A "MP(Rp)/DE dimer synthon refers to a dinucleoside wherein the two nucleosides are linked by a methylphosphonate internucleosidyl linkage of Rp chirality and one of the nucleosides has a 5'- or 3'-coupling group which when coupled to a 3'-OH or a 5'-OH, of another nucleoside or an oligomer will result in a phosphodiester internucleosidyl linkage.

A "MP(Rp)/PS dimer synthon" refers to a dinucleoside wherein the two nucleosides are linked by a methylphosphonate linkage of Rp chirality and one of the nucleosides has a 5'- or 3'- coupling group which when coupled to a 3'-OH or 5'-OH of another nucleoside or an oligomer will result in a phosphorothioate internucleosidyl linkage.

A "MP(Rp)(PS)/DE dimer synthon" refers to a dinucleoside wherein the two nucleosides are linked by a methylphosphonothioate linkage of Rp chirality and one of the nucleosides has a 5'- or 3'- coupling group which when coupled to a 3'-OH or 5'-OH of another nucleoside or an oligomer will result in a phosphodiester internucleosidyl linkage.

A "MP(Rp)/PS$_2$ dimer synthon" refers to a dinucleoside wherein the two nucleosides are linked by a methylphosphonate linkage of Rp chirality and one of the nucleosides has a 5'- or 3'- coupling group which when coupled to a 3'-OH or 5'-OH of another nucleoside or an oligomer will result in a phosphorothioate internucleosidyl linkage.

A "2'-O-methyl MP(Rp)/2'-O-methyl DE dimer synthon" refers to a dinucleoside wherein two 2'-O-methyl nucleosides are linked by a methylphosphonate linkage of Rp chirality and one of the nucleosides has a 5'or 3'-coupling group which when coupled to a 3'OH or 5'OH of another nucleoside or an oligomer will result in a phosphodiester internucleosidyl linkage.

DETAILED DESCRIPTION OF THE INVENTION

The phosphonate internucleosidyl linkages used in oligomers of the present invention contain an lower alkyl group replacing one of the two non-bonding (or non-bridging) oxygens on the phosphorus of a phosphodiester internucleosidyl linkage, the other non-bonding oxygen remains or is alternatively replaced by sulfur. The replacement of oxygen by lower alkyl creates a chiral environment around the phosphorus which can be designated as either Rp or Sp, depending on which of the non-bonding oxygens has been replaced with lower alkyl. The Rp and Sp configurations can be depicted as follows:

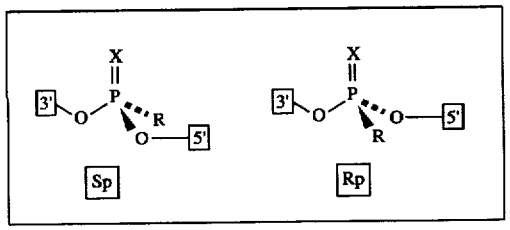

wherein X is oxygen or sulfur and R is lower alkyl. Since the mixed oligomers having phosphonate linkages mixed with non-phosphonate linkages are capable of having either Rp or Sp chirality at each phosphonate linkage, a particular Oligomer theoretically can have $2^n$ different diastereomeric forms where n is the number of phosphonate internucleosidyl linkages in the Oligomer. For example, an Oligomer having 10 phosphonate internucleosidyl linkages theoretically has 1,024 diastereomers and an Oligomer having 18 phosphonate internucleosidyl linkages theoretically has 262, 144 diastereomers.

By providing Oligomers having chirally pure phosphonate linkages mixed with non-phosphonate linkages, the number of diastereomers for a particular Oligomer is decreased. Thus, in one aspect, the present invention is directed to methods of synthesizing Oligomers having chirally pure phosphonate internucleosidyl linkages mixed with non-phosphonate internucleosidyl linkages, and, a particularly preferred aspect, Oligomers having chirally pure Rp-configuration methylphosphonate internucleosidyl linkages mixed with non-phosphonate linkages.

According to one preferred synthetic method, nucleoside dimers having a phosphonate linkage connecting the two nucleosidyl units of the dimer are prepared and separated into their Rp and Sp isomers. The resulting dimers which have a defined chirality at the phosphonate linkage, are then derivatized so that they may be coupled together using an automated DNA synthesizer (see, e.g., Examples 1 to 4). The dimers may have coupling groups which result in any one of a variety of internucleosidyl linkages between dimers. From a stock of 16 dimers, Oligomers of any nucleoside base sequence may be synthesized by linking together the appropriate dimers. Dimers are added to the growing Oligomer chain until an Oligomer having the desired number of nucleosides is obtained. The resulting Oligomer has a defined chirality at every other internucleosidyl linkage (i.e., those linkages originally derived from the coupled dimeric units). The remaining internucleosidyl linkages comprise non-phosphonate internucleosidyl linkages, such as phosphodiester, phosphorothioate, phosphorodithioate, morpholino, phosphoramidite, phosphorofluoridate, boranophosphate, formacetal, silyl or other non-phosphonate internucleosidyl linkages.

Alternatively, larger blocks of nucleosides such as trimers and tetramers may be coupled to give a chirally enriched oligomer. Trimers having two chirally pure internucleosidyl linkages may be conveniently prepared by coupling the appropriate chirally pure dimer synthon to another nucleoside and, for example, if Rp chirality is selected for, then separating the resulting Rp-Rp and Rp-Sp trimers. The resulting trimer has defined chirality (i.e., is chirally pure) at both internucleosidyl linkages. The trimers are then derivatized to give trimer synthons so that they may be coupled together using an automated DNA synthesizer. The trimer synthons have coupling groups which allow them to be coupled together to give a chirally enriched phosphonate oligomer. (See Examples 19 and 20). From a stock of 64 trimers, oligomers of any base sequence may be synthesized by linking together the appropriate trimers. Trimers may be sequentially added to the growing oligomer chain or alternatively coupled with nucleoside monomers, dimers and/or tetramers until an oligomer having the desired number of nucleosides is obtained. The resulting oligomer has a defined chirality at those internucleosidyl linkages derived from the internucleosidyl linkages of the coupled dimers, trimers or tetramers. Thus, use of these trimers will result in an oligomer having phosphonate linkages of defined chirality at about two out of every three internucleosidyl linkages. By following analogous techniques, tetramers having three chirally pure internucleosidyl linkages may be prepared and coupled to each other to give oligomers. Alternatively, dimers, trimers and other short oligomers having internucleosidyl linkages of defined chirality (such as pure Rp) may be coupled together in appropriate sequence to give an oligomer of a particular desired sequence and length.

According to an alternate synthetic method, coupling conditions for nucleoside synthons (or dimers) are used which direct coupling to give an enhanced yield of the desired chiral-configuration. This method may be used to couple individual nucleoside synthons or alternatively the chirally pure dimers and, thus, obtained are Oligomers enriched for the desired chiral configuration at each of the phosphonate internucleosidyl linkages.

The chirally pure methyl phosphonate dimers and trimers taught in the examples and Detailed Description herein can be coupled together by a variety of different methods leading to the following, non-exclusive, types of internucleosidyl linkages: phosphodiester, phosphotriester phosphorothioate, phosphorodithioate, phosphoramidate, phosphorofluoridates, boranophosphates, formacetal, and silyl.

Internucleosidyl phosphodiester linkages can be obtained by converting the 3' OH of a chirally pure dimer or trimer to either a phosphotriester synthon (Reese, C. B. (1978) Tetrahedron 34, 3142–3179), phosphoramidite synthon (Beaucage, S. L. and Lyer, R. P. (1992) Tetrahedron 48, 2223–2311), H-phosphonate synthon (Froehler, B. C. in Agrawal, S., ed. Protocols for Oligonucleotides and Analogs, Synthesis and Properties, Methods in Molecular Biology Vol. 20, Humana Press, Totowa, N.J., 1993, pp. 63–80), or phosphoromonochloriditie reagent (Hogrefe, R. I. (1987) dissertation, Northwestern University, Evanston, Ill.).

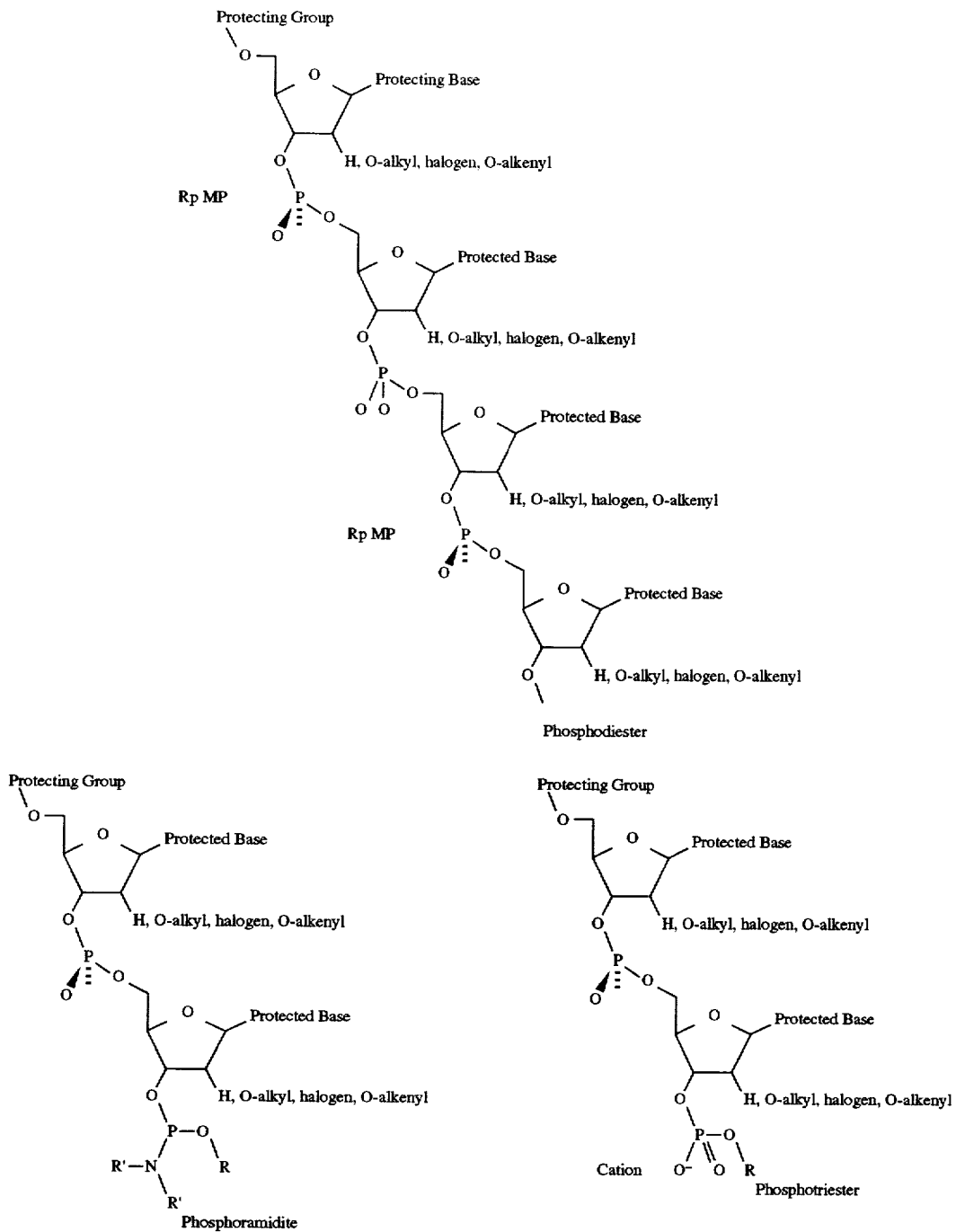

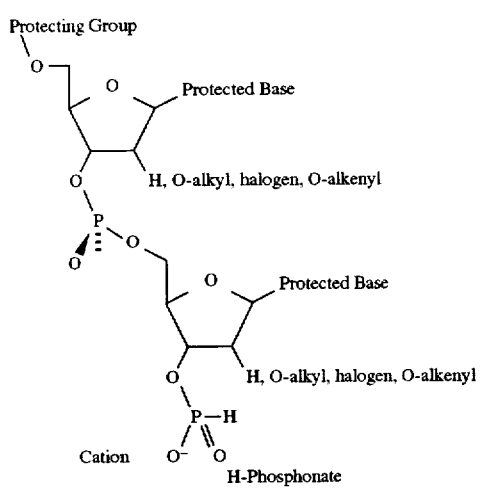

H-Phosphonate

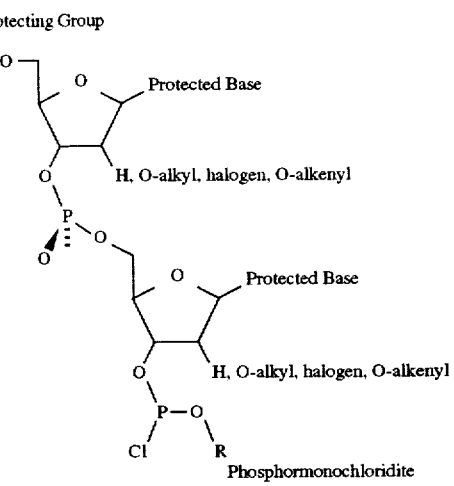

Phosphormonochloridite

Internucleosidyl phosphorothioate linkages can be obtained by converting the 3' OH of a chirally pure dimer or trimer to either a phosphotriester synthon (Stec, W. J., et al. (1991) Nucl. Acids Res. 19, 5883–5888)), phosphoramidite synthon (Lyer, R. P., et al. (1990) JACS 112, 1254–1255), H-phosphonate synthon (Seela, F. and Kretschmer U. (1991) J. Org. Chem. 56, 3861–3869), or phosphoromonochloridite reagent (Hogrefe, R. I. (1987) Dissertation, Northwestern University, Evanston, Ill.).

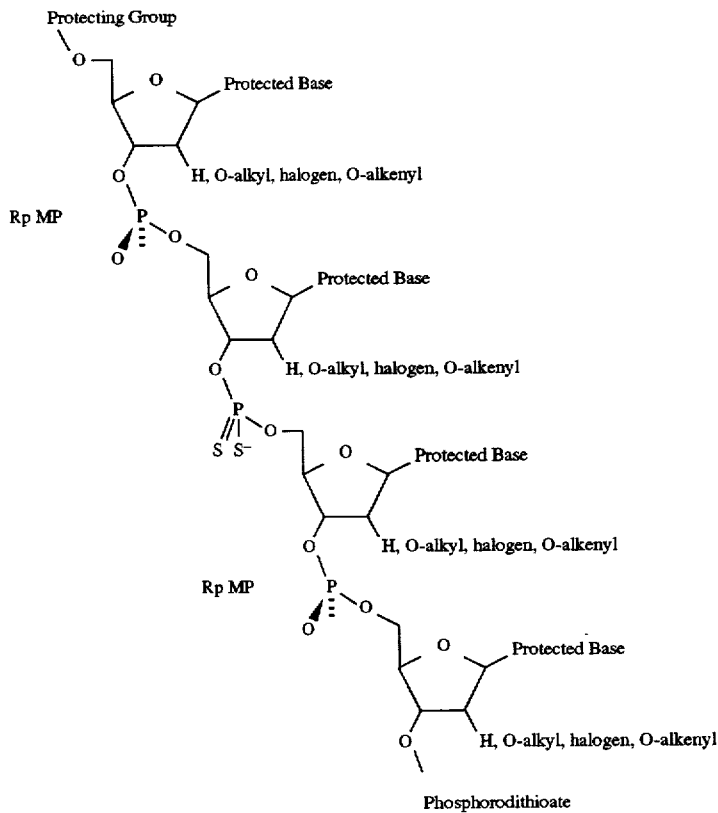

Phosphorodithioate

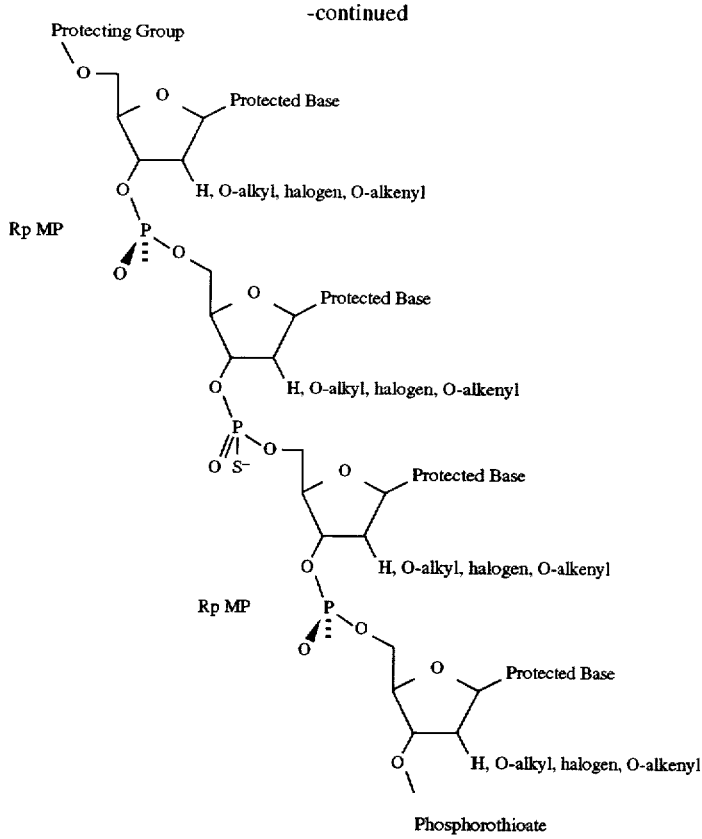

Internucleosidyl phosphorodithioate linkages can be prepared as by the Example herein and by U.S. Pat. No. 5,218,088 to Gorenstein et al. Internucleosidyl phosphotriester linkages can be obtained by converting the 3'-OH of a chirally pure dimer or trimer to either a phosphotriester synthon (Reese, C. B. (1978) Tetrahedron 34, 3143–3179), phosphoramidite synthon (Beaucage, S. L. and Lyer, R. P. (1992) Tetrahedron 48, 2223–2311), H-phosphonate synthon (Froehler, B. C. in Agrawal, S., ed. Protocols for Oligonucleotides and Analogs, Synthesis and Properties, Methods in Molecular Biology Vol. 20, Humana Press, Totowa, N.J., 1993, pp. 63–80), phosphoromonochloridite reagent (Hogrefe, R. I. (1987) Dissertation, Northwestern University, Evanston, Ill.), or post synthetically (see U.S. Pat. No. 5,023,243 to Tullis).

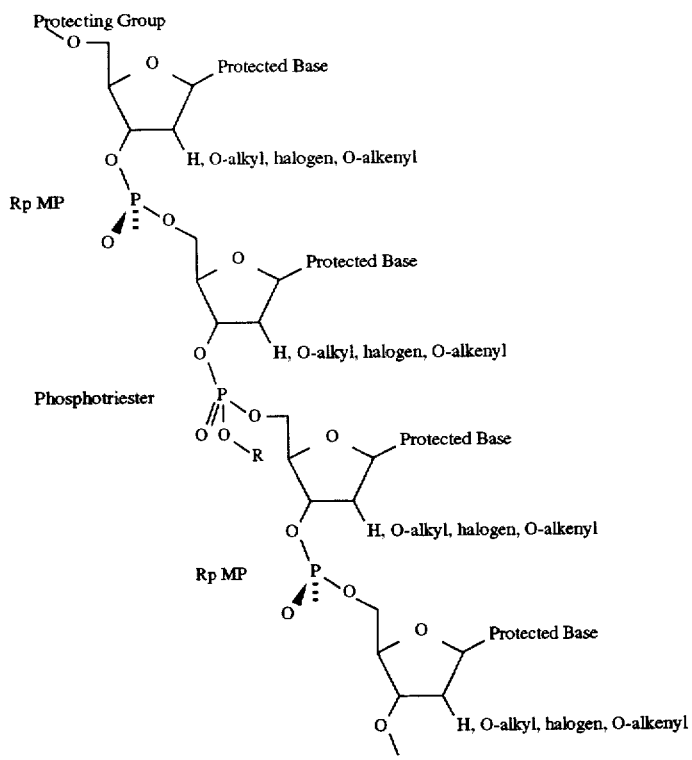

Internucleosidyl phosphoramidate, phosphorofluoridate, boranophosphate, formacetal, and silyl linkages can be obtained by converting the 3' OH of a chirally pure dimer or trimer to the appropriate synthons. (See Agrawal, S., ed. Protocols for Oligonucleotides and Analogs, Synthesis and Properties, Methods in Molecular Biology Vol. 20, Humana Press, Totowa, N.J., 1993, for synthetic protocols to obtain synthons for each of the above.)

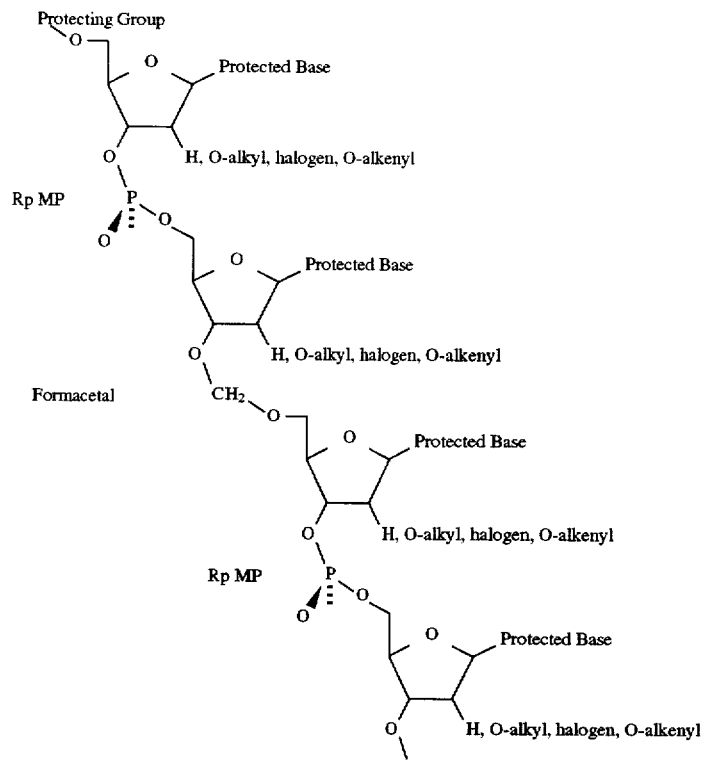
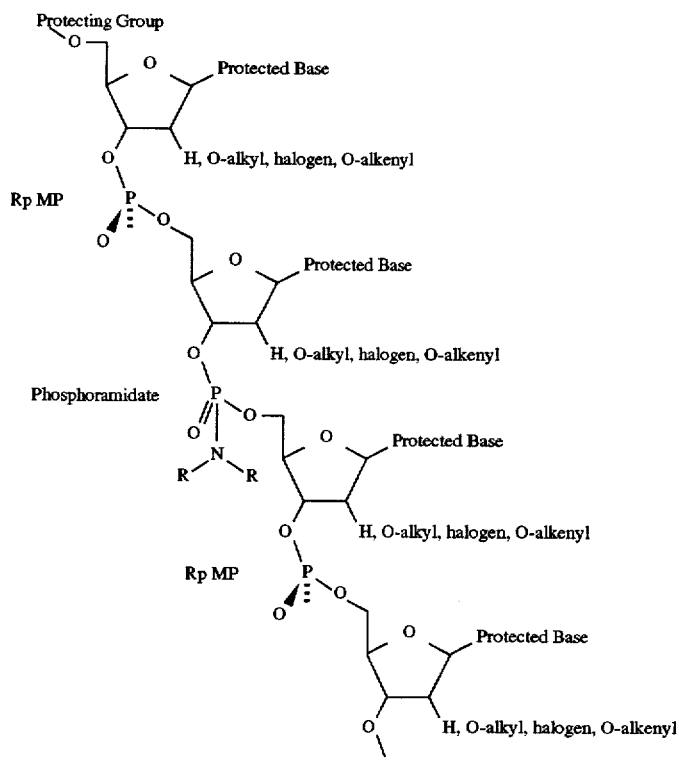

-continued

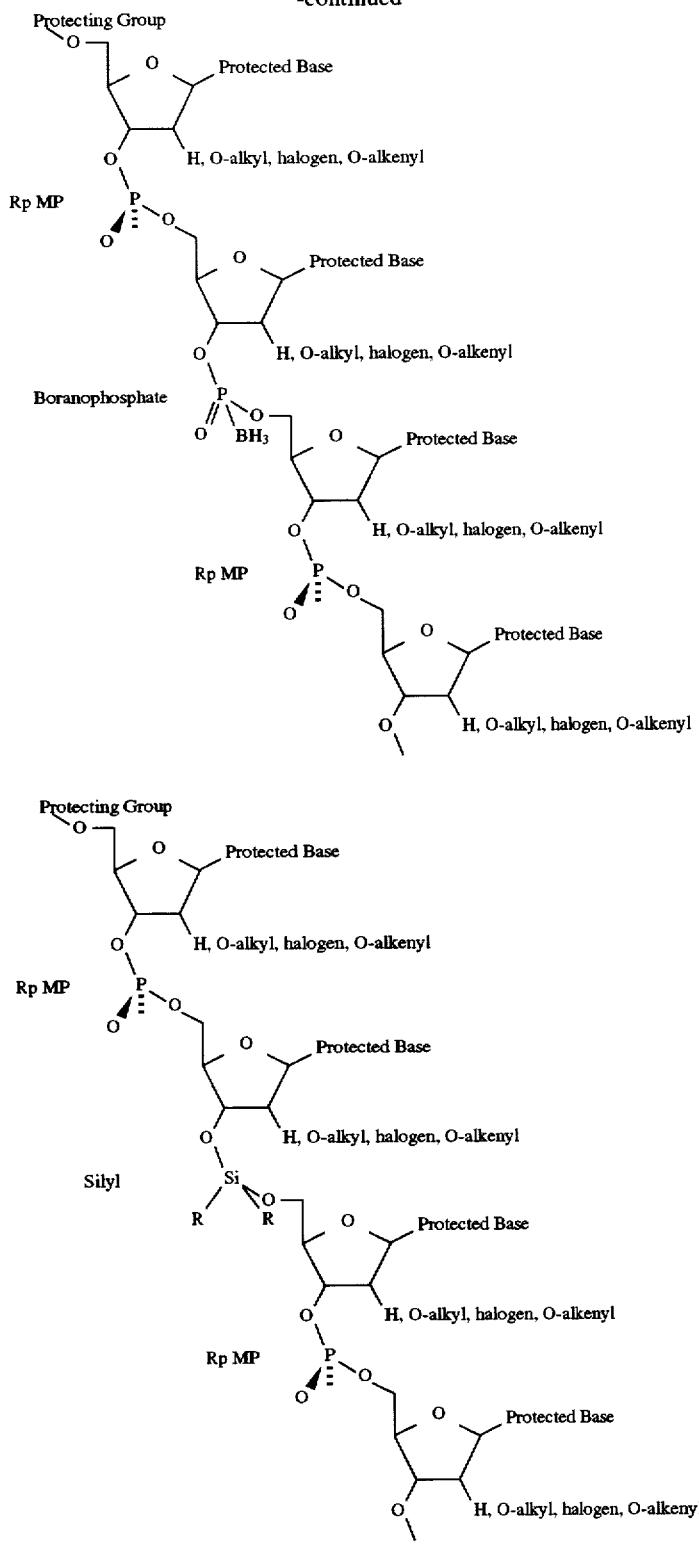

Utility and Administration

The Oligomers provided herein may form a high affinity complex with a target sequence such as a nucleic acid with a high degree of selectivity. In addition, derivatized Oligomers may be used to bind with and then irreversibly modify a target site in a nucleic acid by cross-linking (psoralens) or cleaving one or both strands (EDTA). By careful selection of a target site for cleavage, one of the strands may be used as a molecular scissors to specifically cleave a selected nucleic acid sequence. Alternatively, the Oligomers of the present invention may include an RNase H activating sequence.

According to one aspect of the present invention, these antisense Oligomers have a sequence which is complementary to a portion of the RNA transcribed from a selected target gene. Although the exact molecular mechanism of inhibition has not been conclusively determined, it has been suggested to result from formation of duplexes between the antisense Oligomer and the RNA transcribed from the target gene. The duplexes so formed may inhibit translation, processing or transport of an mRNA sequence.

According to an alternate aspect of the present invention, interference with or prevention of expression or translation of a selected RNA target sequence may be accomplished by triple helix formation using Oligomers of the present invention as a Triplex Oligomer Pair having sequences selected such that the Oligomers are complementary to and form a triple helix complex with the RNA target sequence and thereby interfere with or prevent expression of the targeted nucleic acid sequence. Such triple strand formation can occur in one of several ways. Basically, two separate or connected Oligomers may form a triple strand with the single stranded RNA. Further descriptions of the use of Oligomers (including Triplex Oligomer Pairs) to prevent or interfere with the expression of a target sequence of double or single stranded nucleic acid by formation of triple helix complexes is described in the copending U.S. patent applications Ser. Nos. 07/388,027, 07/751,813, 07/772,081 and 07/987,746, the disclosures of which are incorporated herein by reference.

As a general matter, the Oligomers employed will have a sequence that is complementary to the sequence of the target nucleic acid. However, absolute complementarity may not be required; in general, any Oligomer having sufficient complementarity to form a stable duplex (or triple helix complex as the case may be) with the target nucleic acid is considered to be suitable. Since stable duplex formation depends on the sequence and length of the hybridizing Oligomer and the degree of complementarity between the antisense Oligomer and the target sequence, the system can tolerate less fidelity (complementarity) when longer Oligomers are used. This is also true with Oligomers which form triple helix complexes. However, Oligomers of about 8 to about 40 nucleosidyl units in length which have sufficient complementarity to form a duplex or triple helix structure having a melting temperature of greater than about 40° C. under physiological conditions are particularly suitable for use according to the methods of the present invention.

With respect to single stranded target sequences, we have found that two strands of a methylphosphonate Oligomer having methylphosphonate linkages (Second and Third Strands) and one strand of a complementary synthetic RNA Oligomer (First Strand) may form a triple helix complex. According to those experiments, the two methylphosphonate strands bind in a parallel orientation. Experiments described triple helix formation with methylphosphonate Oligomers of random sequence of A and G nucleosides which would not make triple helix complexes according to any of the "classical" triplet motifs.

These triple helix complexes formed by binding a target single stranded RNA and two methylphosphonate Oligomers show high affinity (Tm>50° C.). Formation of these triple helix complexes has been shown to dramatically inhibit translation at sub-micromolar concentrations.

The triple helix complexes can be formed using Oligomers containing naturally occurring bases (i.e., A, C, G, T or U). Alternatively, if desired for increased stability, certain stabilizing bases such as 2-amino A (for A) or 5-methyl C may be used in place of the corresponding naturally occurring base. These bases may increase stability of the triple helix complex by having increased hydrogen bonding interactions and stacking interactions with other bases. Increased stability may result in increased affinity constants which increase potency.

The Oligomers provided herein may be derivatized to incorporate a nucleic acid reacting or modifying group which can be caused to react with a nucleic acid segment or a target sequence thereof to irreversibly modify, degrade or destroy the nucleic acid and thus irreversibly inhibit its functions.

These Oligomers may be used to inactivate or inhibit or alter expression of a particular gene or target sequence of the same in a living cell, allowing selective inactivation or inhibition or alteration of expression. The target sequence may be DNA or RNA, such as a pre-mRNA or an mRNA. mRNA target sequences include an initiation codon region, a coding region, a polyadenylation region, an mRNA cap site or a splice junction. These Oligomers could also be used to permanently inactivate, turn off or destroy genes which produced defective or undesired products or if activated caused undesirable effects.

Since the Oligomers provided herein may form duplexes or triple helix complexes or other forms of stable association with transcribed regions of nucleic acids, these complexes are useful in "antisense" or triple strand therapy. "Antisense" therapy as used herein is a generic term which includes the use of specific binding Oligomers to inactivate undesirable DNA or RNA sequences in vitro or in vivo.

Many diseases and other conditions are characterized by the presence of undesired DNA or RNA, which may be in certain instances single stranded and in other instances in double stranded. These diseases and conditions can be treated using the principles of antisense therapy as is generally understood in the art. Antisense therapy includes targeting a specific DNA or RNA target sequence through complementarity or through any other specific binding means, in the case of the present invention by formation of duplexes or triple helix complexes.

The Oligomers for use in the instant invention may be administered singly, or combinations of Oligomers may be administered for adjacent or distant targets or for combined effects of antisense mechanisms with the foregoing general mechanisms.

In therapeutic applications, the Oligomers can be formulated for a variety of modes of administration, including oral, topical or localized administration. It may be beneficial to have pharmaceutical formulations containing acid resistant Oligomers that may come in contact with acid conditions during their manufacture or when such formulations may themselves be made acidic, to some extent, in order to more compatible with the conditions prevailing at the site of application, e.g., the acid mantle of the skin. Techniques and formulations generally may be found in *Remington's Pharmaceutical Sciences*, Mack Publishing Co., Easton, Pa., latest edition. The Oligomer active ingredient is generally combined with a carrier such as a diluent or excipient which may include fillers, extenders, binding, wetting agents, disintegrants, surface-active agents, erodible polymers or lubricants, depending on the nature of the mode of administration and dosage forms. Typical dosage forms include tablets, powders, liquid preparations including suspensions, emulsions and solutions, granules, and capsules.

Certain of the Oligomers of the present invention may be particularly suited for oral administration which may require exposure of the drug to acidic conditions in the stomach for up to about 4 hours under conventional drug delivery conditions and for up to about 12 hours when delivered in a sustained release from. For treatment of certain conditions it may be advantageous to formulate these Oligomers in a sustained release form. U.S. Pat. No. 4,839,177 to Colombo et al., the disclosure of which is incorporated herein by reference, describes certain preferred controlled-rate release systems. For oral administration, these Oligomers have 2'-O methyl [alkyl?] nucleosidyl units; these Oligomers are formulated into conventional as well as delayed release oral administration forms such as capsules, tablets, and liquids.

The Oligomers having 2'-O-alkyl nucleosidyl units may be particularly suited for formulation in preparations for topical administration, since the skin has an acid mantle, formulations including these acid resistant Oligomers may prove advantageous. This also can be advantageous in light of the finding that neutral Oligomers will cross skin and mucous membranes as described in U.S. patent application Ser. No. 07/707,879 which is incorporated by reference. Also it may be desirable to provide formulations which include acidic media when using acid-resistant neutral Oligomers.

For topical administration, the Oligomers for use in the invention are formulated into ointments, salves, eye drops, gels, or creams, as is generally known in the art.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucusal administration. In addition, detergents may be used to facilitate permeation. Transmucosal administration may be through use of nasal sprays, for example, as well as formulations suitable for administration by inhalation, or suppositories.

To assist in understanding the present invention, the following examples are included which describe the results of a series of experiments. The following examples relating to this invention should not, of course, be construed in specifically limiting the invention and such variations of the invention, now known or later developed, which would within the purview of one skilled in the art are considered to fall within the scope of the present invention as hereinafter claimed.

EXAMPLES

EXAMPLE 1

Preparation of a MP(Rp)/DE Dimer Synthon
A. Preparation of a (CT) Dimer Having a Chirally Pure Methylphosphonate Internucleosidyl Linkage Using Solution Phase Chemistry Into a 2 L roto-evaporator flask was placed 10.0 g (28 mM) of 3'-tert-butyldimethylsilyl thymidine and 26.1 g (35 mM) of 5'-dimethoxytrityl-$N^4$-isobutyryl-3'-methyl-N,N-diisopropylaminophosphoramidite-2'-deoxycytidine. The solids were dissolved in 500 ml of acetonitrile and evaporated to dryness under vacuum. This process was repeated with another 500 ml of acetonitrile and then the flask was released under argon and stoppered with a rubber septa.

This dry solid foam was then dissolved in 500 ml of acetonitrile ("ACN"), and with manual stirring, treated all at once with 404 ml tetrazole (180 mM, 0.45M tetrazole in THF). Manual stirring is continued for 30 seconds and then the flask is allowed to stand for another 2.5 minutes, after which time the reaction mix is treated all at once with 275 ml of an oxidizer solution ($I_2$/$H_2O$/lutidine/THF; 25 g/2.5 ml/100 ml/900 ml). The solution was stirred manually and allowed to stand at room temperature for 15 minutes. The resulting dark amber solution was then treated with bisulfite (2 g/25 ml/$H_2O$), which upon addition, turned the solution light amber as it reacted with the excess iodide. The reaction mix was then concentrated to a thick oil and taken up in ethyl acetate ("EtOAc") (500 ml) and washed with saturated sodium bicarbonate (2×250 ml) and $H_2O$ (2 ×250 ml). The organic phase was dried over $MgSO_4$, filtered and concentrated to a light colored solid foam, which upon further drying yielded 35 grams of crude dimer.

The crude dimer was run on HPLC (reverse phase, Waters C18 bondapak) with a program (ACNMETH) starting with 50% acetonitrile and 0.1M triethylammonium acetate (TEAA, pH~7.0) which increased to 100% acetonitrile over 20 minutes with a linear gradient. Two major peaks were resolved, one at 14.5 minutes, which is residual lutidine and the other at 14.5 minutes which is the mixture of Rp and Sp diastereomers. The ratio of Rp and Sp was determined quantitatively by taking a 5 mg aliquot of the crude product and dissolving it in 1.5 ml of acetonitrile along with 0.5 ml of tetrabutylammonium fluoride (TBAF, 1M solution in THF). After standing at room temperature for 10 minutes the sample was run on HPLC. Two new peaks were observed at 6.5 and 7.1 minutes and the later eluting peak was gone. The first new peak, which is believed to be the Sp diastereomer, represented 66% (2/1) of the normalized value for the two peaks. The crude product was also analyzed by the (normal phase silica plate) in 75/25 EtOAc/$CH_2Cl_2$ ("75/25") with 5% methanol added. The tlc showed two spots with Rf's of 0.45 and 0.64, respectively; the faster running product (believed to be the Rp form) was less intense than the slower moving one.

The Rp diastereomer was separated on normal phase silica using a methanol step gradient in 75/25 EtOAc/$CH_2Cl_2$. A 7.5 cm by 60 cm column, was loaded with 700 g of silica (first slurried in 2.5 L of neat 75/25 EtOAc/$CH_2Cl_2$). The crude dimer was then dissolved in 75 ml of 75/25 EtOAc/$CH_2Cl_2$ and loaded onto the column. The column was started with 1% methanol and increased to 2% and finally 3% where the Rp dimer began to elute. The Rp dimer eluted cleanly over several bed volumes while maintaining 3% methanol in the eluent. The Sp dimer was eluted later with 30% methanol. The Rp dimer yield was 11.0 grams, while the Sp yield was 17.8 grams. HPLC analysis (ACNMETH) was performed on the Rp dimer and one peak was observed at 14.5 minutes. The tlc (75/25 EtOAc/$CH_2Cl_2$, 5% methanol) of this product, revealed a single spot product with an Rf of 0.55 which, upon treatment with 10% sulfuric acid in ethanol and heat, was both trityl and sugar positive.

The newly resolved Rp dimer, 11.0 g (0.011M) was dissolved in 110 ml of ACN and treated all at once at room temperature with 22 ml of TBAF (0.022M, 1M in THF). The reaction mixture was allowed to stand overnight at ambient temperature. The next morning the reaction was determined to be complete by tlc (75/25, EtOAc/$CH_2Cl_2$ with 10% methanol), no starting material was detected but a small amount of 5'-DMT-dT was observed, which runs considerably faster on normal phase silica than the 3'-OH of the dimer. The reaction mixture was concentrated on a rotary evaporator to a thick oil which was then dissolved in $CH_2Cl_2$ (200 ml) and washed with saturated sodium bicarbonate (2×100 ml) and $H_2O$(2×100 ml). The organic phase was dried over $MgSO_4$, filtered, and concentrated to a light yellow solid foam, which was purified on 100 grams of silica (75/25, EtOAc/CH$_2$Cl$_2$ with 5% methanol). The 5'-DMT-dT was removed but an impurity at 13.5 minutes (HPLC, ACNMETH) was detected which was first believed to be unreacted starting material (t-BDMS on) but after additional treatment with TBAF this was found not to be the case. A second column, using 100 g of silica and the same eluent was run and smaller fractions were taken; the column was able to successfully separate the two spots. The pure CT-Rp dimer fractions were pooled and concentrated to yield 5.5 grams of a nearly white solid foam.

B. Preparation of a Chirally Pure (CT) MP/DE Dimer Synthon

Into a 100 ml round bottom flask was placed 0.5 g (0.55 mMol) CT-3'-OH dimer (product of Example 1A) which was rendered anhydrous by 3×20 ml co-evaporations with pyridine. The flask was released from the vacuum system under argon gas and stoppered with a rubber septa. The compound was redissolved in 10 ml acetonitrile and 200 µl (1.4 mMol, 2.5 eq) TEA were added. To the resulting mixture at room temperature and with manual stirring, was added in one portion 200 µl (0.90 mmol, 1.6 eq.) 2'-cyanoethyl-N, N-diisoprophylchlorophosphoramidite. The reaction mixture was allowed to sit at room temperature before being analyzed by reverse phase HPLC. The HPLC (Beckman System Gold, C18 bondapak, ACN method Solution A was 50/50 ACN/0.1M TEAA in water, pH 7 and Solution B was ACN. A gradient of 0 to 100% Solution B was run at a rate of 1 ml/minute over 25 minutes) showed complete conversion of starting material and a crude purity of greater than 90 percent. The diastereomers of the phosphoramidite were not resolved. The reaction mixture was concentrated under vacuum to a light yell solid foam. The foam was purified immediately by chromatography on 20 g of normal flash grade silica equilibrated with 5/1/5 ethyl acetate/acetonitrile/methylene chloride with 2% TEA to give 0.5 g (82% yield) of the above-identified product as an off-which solid foam having a purity of 99.3% as determined by HPLC.

EXAMPLE 2

Preparation of 2'-O-Methyl MP(Rp)/2'-O-Methyl DE Dimer Synthons

A. Preparation of 2'-O-Methyl C Monomer

A 5.0 g (8 mmol) portion of 2'-O methyl cytidine was rendered anhydrous with pyridine co-evaporations (3×25 ml) and then dissolved in 50 ml acetonitrile. The solution was treated with 1.65 ml triethylamine ("TEA") (12 mmol, 1.5 eq.) and cooled in an ice bath. The solution was then treated with dropwise addition of 1.65 ml chloromethyl-N, N-diisopropylamino phosphine ("Cl-MAP") over two minutes. The ice bath was removed and the reaction mixture stirred for two hours. The reaction mixture (reaction was determined to be complete by HPLC) was concentrated to dryness. The residue was dissolved in 20 ml ethyl acetate/heptane (1:1) with 4% TEA, then loaded onto 40 g silica gel equilibrated with the same solvent system. All UV absorbing eluent from the column was collected and pooled, then concentrated to give 5.5 g of the above-identified product (yield about 90%).

B. Preparation of Silyl-Protected 2'-O-Methyl Uridine

Into a 250 ml round bottom flask was placed 5.0 g (9.0 mmol) 5'-DMT, 2'O-methyl uridine which was rendered anhydrous with dimethylformamide (DMF) co-evaporations (3×25 ml). The resulting dry foam was taken up in 50 ml DMF, then treated all at once with 2.4 g (35 mmol, 3.9 eq.) imidazole, followed by dropwise addition of 3.0 ml (12 mmol, 1.3 eq.) t-butyldiphenylsilyl chloride. The reaction mixture was stirred at room temperature overnight.

The progress of the reaction was checked by HPLC (ACN method) and thin layer chromatography ("TLC") using 5% methanol in methylene chloride, and determined to be complete (no starting material was evident). The reaction mixture was then poured into ice water and taken up in methylene chloride, then washed several times with aqueous sodium bicarbonate and water. The organic phase was dried over magnesium sulfate, filtered and then concentrated to give 7.2 g of a solid foam which gave a single spot on TLC. The solid foam was then dissolved in 70 ml methylene chloride and treated (with rapid magnetic stirring) all at once with 70 ml. benzene sulfonic acid, 2% by weight in 2:1 methylene chloride/methanol. After stirring for 15 minutes at room temperature, the reaction mixture was quenched with 10 ml TEA. The resulting detrilylated compound was stripped down to a thick amber oil which was then loaded onto 150 g. silica gel equilibrated in heat methylene chloride. The product was eluted from the column using 2% methanol (in methylene chloride). After drying, 3.51 g of the above identified product were obtained (yield about 80%).

C. Preparation of 2'-O-Methyl (CU) Dimer

The silyl-protected 2'-O methyl uridine monomer (product of Example 2B) (3.0 g, 6 mmol) was taken up in 30 ml anhydrous ACN. The 2'-O methyl cytidine amidite monomer (product of Example 2A) (5.5 g, 7 mmol, 1.2 eq.) separately, was taken up in 55 ml ACN. Both solutions were allowed to stand over 3 Å molecular sieves overnight at room temperature.

The two solutions were carefully decanted into a single flask and treated with 94 ml tetrazole (0.45M in ACN, 42 mmol, 7 eq). The resulting mixture was stirred for 4 minutes and then oxidized by addition of 1.5 ml (1.2 eq.) cumene hydroperoxide. The reaction mixture was concentrated to dryness, then taken up in methylene chloride and washed with aqueous sodium bicarbonate and water. The organic phase was dried over magnesium sulfate, filtered and concentrated to give 7.5 g. of a solid foam. The diastereomeric ratio as determined by HPLC by comparison of areas under peaks was 57/43 Sp to Rp.

The Rp diastereomer was isolated by column chromatography using two silica columns (100:1, silica to crude product, equilibrated in 3:1 ethylacetate/methyl chloride with an increasing methanol gradient from 1 to 5%). A total of 1.07 g of pure Rp dimer was isolated.

D. Deprotection of 2'-O-Methyl (CU) Dimer

A 1.07 g (0.90 mmol) portion of the 2'-O methyl CU dimer (product of Example 2C) was dissolved in 10 ml THF and treated all at once with 1.5 ml (1 m in THF, 1.5 eq.) tetrabutylammonium fluoride ("TBAF"). The reaction mixture was stirred at room temperature of r 30 minutes after which time HPLC revealed complete deprotection of the silyl group had been achieved. The reaction mixture was concentrated and the concentrate purified on 10 g silica gel, eluting with 3:1 ethyl acetate/methylene chloride with 5% methanol. The clean fractions were concentrated to give 550 mg of the above-identified pure 5'-OH dimer.

E. Preparation of a Chirally Pure 2'-O-Methyl (CU) (MP/DE) Dimer Synthon

A 230 mg portion of 2'-O-methyl CU 3'-OH dimer (product of Example 2D) was rendered anhydrous by 2×5 ml co-evaporations in ACN. The resulting dry solid foam was dissolved in 2.5 ml ACN and then 73 µl (2.5 eq.) triethylamine ("TEA") and 94 µl (2.0 eq.) 2'-cyanoethyl-N, N-diisopropyl chlorophosphoramidite (βCNE) were added. The reaction mixture was stirred at room temperature for 2 hours at which time HPLC analysis determined the reaction to be complete. The reaction mixture was dissolved in eluent (3/1/1 ethylacetate/acetonitrile/methylene chloride with 4% TEA) and loaded onto 2 g silica gel equilibrated with 3/1/1 ethylacetate/acetonitrile/methylene chloride with 4% TEA. The column was run using 3/1/1 ethylacetate/acetonitrile/ methylene chloride with 1% TEA. The clean fractions, 3 to 25, were concentrated, redissolved in acetonitrile and concentrated again to a solid foam. The foam was dried overnight under full vacuum to give 200 mg of the above-identified product.

EXAMPLE 3

Preparation of 2'-O Methyl MP(Rp)(PS)/ 2'-O Methyl-DE Dimer Synthons

These dimer synthons are prepared by following the procedures described in Example 2, except that in Paragraph C, an equivalent amount of 3H-1,2-benzodithiole-3-one, 1,1-dioxide (Beaucage reagent) is substituted for cumene hydroperoxide.

EXAMPLE 4

Preparation of MP(Rp)(PS)/DE Dimer Synthons

These dimer synthons are prepared by following the procedures of Example 1, except in Paragraph A, an equivalent amount 3-H-1,2-benzodithiole-3-one, 1,1-dioxide (Beaucage reagent) is substituted for the oxidizer solution ($I_2/H_2O$/lutidine/THF).

EXAMPLE 5

Preparation of MP(Rp)/PS, Dimer Synthons

The MP/(Rp)/$PS_2$ (phosphorodithioate) dimer synthons are prepared as follows.

Isometrically pure Rp dinucleosides having a free 3'-OH are prepared according to the methods described in Examples 1A.

The dinucleoside is converted to the corresponding thiophosphoramidite using procedures such as those of Plotto et al. (Plotto et al, Tetrahedron 47:2449–61 (1991)) or Gorenstein et al., U.S. Pat. No. 5,218,088.

The dinucleoside is co-evaporated three times with anhydrous pyridine, followed by three co-evaporations with toluene.

A portion of dinucleoside (10 mmoles) is dissolved in 200 ml anhydrous dichloromethane, then three equivalents of anhydrous diisopropylethylamine followed by 1.5 equivalents of chloro-N,N-diisopropylaminothiomethoxyphosphine are added at 0° C. with stirring. The reaction is monitored by TLC until determined to be complete.

The product is worked up and purified using the procedures of Example 1B for isolation of the MP(Rp)/DE phosphoramidite.

EXAMPLE 6

Preparation of MP(RI)(PS)/PS) Dimer Synthons

The MP(Rp)(PS)/$PS_2$ dimer synthons are prepared as follows. The isometrically pure Rp dinucleoside with a free 3'-OH is prepared according to the methods of Example 4. Using the dinucleoside, the dimer synthon is prepared by the methods of Example 5.

EXAMPLE 7

Preparation of MP(Rp)(PS)/2'-O Methyl DE Dimer Synthons

The MP(Rp)(PS)/2'-O-methyl DE dimer synthons are prepared using procedures analogous to those of Examples 1 and 3 but using the appropriate protected 2'-deoxynucleoside and protected 2'-O-methyl nucleosides.

EXAMPLE 8

Preparation of an Oligomer Having Alternating MP (Rp)/DE Internucleosidyl Linkages An oligomer having the sequence 5'-(C*T)-(C*T)-(C*T) -(C*T)-(C*T)-(C*T)-(C*T)-A-3' was prepared using a C*T MP(Rp)/DE dimer synthon prepared according to Example 1. The grouped dinucleosides indicate where the stereochemistry is fixed as the fast eluting isomer on silica gel (putative Rp) and the asterisks indicate the chirally pure linkages.

Manual couplings were used to synthesize the oligomer to conserve reagent, although the process can be done on an automated DNA synthesizer. The sequence was synthesized from the 3'-terminus starting with methacrylate support bound deoxyadenosine.

The protected dinucleoside methylphosphonamidite (22 mg each per required coupling) freshly co-evaporated with pyridine and toluene to ensure dryness were placed into dried 1 ml glass autosampler vials and dissolved in anhydrous acetonitrile to a concentration of 0.1M (200 µl per coupling). The vessels were purged with argon and tightly sealed with screw caps with teflon septa.

A 1 µmole scale DNA synthesis column (Milligen) was filled with 1 µmole of methacrylate support bound deoxyadenosine. The column was attached to a ring stand in a vertical orientation. A male-male leur fitting was attached to the bottom along with an 18 gauge needle to control the effluent. The column was washed with 10 ml acetonitrile using a syringe. The support bound nucleoside was detritylated by passing 3 ml of 2% dichloroacetic acid in dichloromethane through the column over 1.5 minutes. The orange, dimethoxytrityl cation bearing solution was reserved. The column was washed twice with 10 ml each of anhydrous acetonitrile.

The first coupling was accomplished as follows: 10 ml more anhydrous acetonitrile was passed through the column. Then, 200 µl of the CT methylphosphonamidite was drawn into a 1 ml syringe. Next, 200 µl of 0.45M tetrazole in anhydrous acetonitrile was likewise drawn into the syringe containing the methylphosphonamidite. The reagents were rapidly mixed in the syringe, then slowly passed through the column dropwise over three minutes, being sure to lightly draw the plunger up and down to ensure adequate mixing with the support. After 3 minutes, 1 ml of the oxidizing reagent (0.1M $I_2$ in 73% tetrahydrofuran, 25% 2,6-lutidine and 2% water) was passed through the column over one minute. The column was washed with 20 ml acetonitrile and then treated with 600 µl of a solution containing 20% (v/v) acetic anhydride, 30% (v/v) acetonitrile, 50% (v/v) pyridine and 0.312% (w/v) dimethylaminopyridine. The column was then washed with 20 ml acetonitrile.

The above-described synthetic cycle was repeated until the synthesis was completed. The overall coupling efficiency based on dimethoxytrityl absorbance was 95.7%, for an average of 99.3% per coupling.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed to sit for 6 hours at ambient temperature in order to go to completion. The supernatant containing the oligomer was then removed from the support and the support was rinsed twice with 2 ml of 1/1 acetonitrile/water; the washings were combined with the supernatant. The combined solution was diluted to 30 ml total volume with water and neutralized with approximately 4 ml of 6N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column, it was washed with 30 ml of water. The product was then eluted with 5 ml of 1/1 acetonitrile/water.

The oligomer was purified on HPLC using a Beckman Ultrasphere-reverse phase 4.5×250 mm column with an increasing gradient of acetonitrile in 0.5M triethylammonium acetate (0% to 40% over 40 minutes). The isolated yield was 41 $OD_{260}$ units (35%). The compound was characterized by electron spray mass spectrometry (calc. 4391/ found 4391).

Alternatively, the above-identified oligomer can be synthesized on an automated DNA synthesizer. In which case the appropriate dimer synthons (as used above in the manual synthesis) are dissolved in acetonitrile to a concentration of 0.1M as described above. The amidite solutions are placed in conical vessels on a Millipore Expedite DNA Synthesizer. All other reagents (oxidizer, deblock, capping reagents and activator) are prepared as described above for the manual synthesis, and applied to the appropriate positions on the instrument as instructed in the manual. Table I gives programming parameters for one synthesis cycle. The deprotection and purification of the oligomer is carried as described above for the manually synthesized oligomer.

EXAMPLE 9

Preparation of an Oligomer Having Alternating 2'-O-Methyl MP(Rp)/2'-O-Methyl DE Internucleosidyl Linkages An oligomer having the sequence 5'(C*U)-(C*U)-(C*U)-(C*U)-(C*U)-(C*U)-(C*)-A-3' was prepared using 2'-O-methyl MP(Rp)/2'-O-methyl DE dimer synthons prepared according to Example 2 hereinabove.

The appropriate dimer synthons were dissolved in acetonitrile to a concentration of 0.1M. All other reagents used were as described in Example 8.

A 1 μmole scale DNA synthesis column (Millipore) was filled with 1 μmole of methacrylate support bound deoxyadenosine. The dimer synthons were coupled sequentially from the 3'-terminus as described in Example 8 except that the coupling time was extended to two minutes. The overall coupling efficiency based on dimethoxytrityl absorbance was 50%, for an average of 91% per coupling, the dimethoxytrityl was removed from the oligomer at the end of the synthesis.

The deprotection was carried out as described in Example 8. The crude yield was 103 $OD_{260}$ units. The oligomer was purified on HPLC with a Beckman Ultrasphere-RP using an increasing gradient of acetonitrile in 0.5M triethylammonium acetate (10% to 30% over 30 minutes). The isolated yield was 39 $OD_{260}$ units (38%). The compound was characterized by electron spray mass spectrometry (calc. 4713/ found 4712).

This oligomer can also be synthesized on an automated DNA synthesizer as follows. The appropriate dimer synthons (as used above in the manual synthesis are dissolved in acetonitrile as described in Example 8. The amidite solutions are placed in conical vessels on the Millipore

TABLE I

| Function | Mode | Amount/ Arg1 | Time(sec)/ Arg2 | Description |
|---|---|---|---|---|
| $Deblocking | | | | |
| 144 /* Advance Frac | */ NA | 1 | 0 | "Event out ON" |
| 0 /* Default | */ WAIT | 0 | 1.5 | "Wait" |
| 141 /* Photometer S | */ NA | 1 | 1 | "START data collection" |
| 16 /* Dblk | */ PULSE | 10 | 0 | "Dblk to column" |
| 16 /* Dblk | */ PULSE | 100 | 49 | "Deblock" |
| 38 /* Wsh A to C1 | */ PULSE | 80 | 0 | "Flush system with Wsh A" |
| 39 /* Gas A to C1 | */ PULSE | 20 | 0 | "Gas A to C1 waste" |
| 141 /* Photometer S | */ NA | 0 | 1 | "STOP data collection" |
| 144 /* Advance Frac | */ NA | 2 | 0 | "Event out OFF" |
| $Coupling | | | | |
| 1 /* Wsh | */ PULSE | 5 | 0 | "Flush system with Wsh" |
| 2 /* Act | */ PULSE | 5 | 0 | "Flush system with Act" |
| 25 /* 8 + Act | */ PULSE | 6 | 0 | "Monomer + Act to column" |
| 25 /* 8 + Act | */ PULSE | 1 | 8 | "Couple monomer" |
| 2 /* Act | */ PULSE | 4 | 31.9 | "Couple monomer" |
| 1 /* Wsh | */ PULSE | 7 | 55.9 | "Couple monomer" |
| 1 /* Wsh | */ PULSE | 8 | 0 | "Flush system with Wsh" |
| $Capping | | | | |
| 12 /* Wsh A | */ PULSE | 20 | 0 | "Flush system with Wsh A" |
| 13 /* Caps | */ PULSE | 8 | 0 | "Caps to column" |
| 12 /* Wsh A | */ PULSE | 6 | 15 | "Cap" |
| 12 /* Wsh A | */ PULSE | 14 | 0 | "Flush system with Wsh A" |
| $Oxidizing | | | | |
| 17 /* Aux | */ PULSE | 15 | 0 | "Aux Ox for b-CE" |
| 12 /* Wsh A | */ PULSE | 15 | 0 | "Flush system with Wsh A" |
| $Capping | | | | |
| 13 /* Caps | */ PULSE | 7 | 0 | "Caps to column" |
| 12 /* Wsh A | */ PULSE | 50 | 0 | "Wsh A" |
| 12 /* Wsh A | */ PULSE | 100 | 0 | "End of cycle wash" |

Expedite DNA synthesizer. All other reagents (oxidizer, deblock, capping reagents and activator) are prepared as described in Example 8, and are applied to the appropriate positions on the instrument as instructed by the manual. The same coupling program as described in Example 8 is used except that the coupling time is extended to 2 minutes.

The deprotection is carried out as described in Example 8. The oligomer can be purified on HPLC using as described above for the manual synthesis.

EXAMPLE 10

Preparation of an Oligomer Having Alternating MP (Rp)/PS Internucleosidyl Linkages An oligomer having alternating MP(Rp)/PS internucleosidyl linkages is prepared using the dimer synthons used in Example 8. All the parameters of the synthesis, deprotection and purification are as described in Example 8, except that the oxidizing reagent is replaced by a 0.1M solution of 3H-1,2-benzodithiole-3-one, 1,1-dioxide or a 0.1M solution of sulfur in 1/1 carbon disulfide/diisopropylethylamine.

EXAMPLE 11

Preparation of an Oligomer Having Alternating MP(Rp) (PS)/DE Internucleosidyl Linkages An oligomer having alternating MP(Rp)(PS)/DE internucleosidyl linkages is prepared using the dimer synthons of Example 4. All other parameters of synthesis, deprotection and purification are as described in Example 8.

EXAMPLE 12

Preparation of an Oligomer Having Alternating MP (Rp)(PS)/PS Internucleosidyl Linkages An oligomer having alternating MP(Rp)(PS)/PS internucleosidyl linkages is prepared using the dimer synthons of Example 4. All of the parameters of synthesis, deprotection and purification are as described in Example 8, except that the oxidizing reagent is replaced by a 0.1M solution of 3H-1,2-benzodithiole-3-one, 1,1-dioxide or a 0.1M solution of sulfur in 1/1 carbon disulfide/diisopropylethylamine.

EXAMPLE 13

Preparation of an Oligomer Having Alternating MP (Rp)/PS$_2$ Internucleosidyl Linkages An oligomer having alternating MP(Rp)/PS$_2$ internucleosidyl linkages is prepared using the dimer synthons of Example 5. All of the parameters of synthesis, deprotection and purification are as described in Example 12.

EXAMPLE 14

Preparation of an Oligomer Having Alternating MP (R)(PS)/PS Internucleosidyl Linkages An oligomer having alternating MP(Rp)(PS)/PS$_2$ internucleosidyl linkages is prepared using the dimer synthons of Example 6. All of the parameters of synthesis, deprotection and purification are as described in Example 12.

EXAMPLE 15

Preparation of an Oligomer Having Alternating MP (Rp)/2'-O-Methyl DE Internucleosidyl Linkages An oligomer having alternating MP(Rp/2'-O-Methyl DE internucleosidyl linkages is prepared using the dimer synthons of Example 7. All other parameters of synthesis, deprotection and purification are as described in Example 9.

EXAMPLE 16

Preparation of 2'-F Dimer Synthons

Dimer synthons useful in the preparation of the oligomers of the present invention may be prepared using 2'-fluoronucleosides. Methods for preparation of 2'-fluoronucleosides have been reported and are known to those skilled in the art. (See, e.g.: Codington, JOC Vol. 29 (1964) (2'-F U); Mangel, Angew. Chem. 96:557–558 (1978) and Doen, JOC 32:1462–1471 (1967) (2'-F C); Ikehara, Chem. Pharm. Bull. 29:1034–1038 (1981) (2'-F G); Ikehara, J. Carbohydrates, Nucleosides, Nucleotides 7:131–140 (1980) (2'-F A), and also Krug, A, Nucleosides & Nucleotides 8:1473–1483 (1989).

The preparation of dimer synthons using 2'-fluoronucleosides may be accomplishing using the procedures analogous to those described for the 2'-O-methyl dimer synthons (See, e.g., Examples 2, 3, and 5). The resulting dimer synthons may be used to prepare oligomers using methods analogous to the methods used for the 2'-O methyl dimer synthons such as Examples 9 and 15.

EXAMPLE 17

Preparation of 2'-O-Alkyl Dimer and Trimer Synthons and Their Use in Oligomer Synthesis The dimer and trimer synthons described in Examples 1, 4 and 14 can be prepared using 2'-O-alkyl nucleosides. The preparation of 2'-O-alkyl nucleosides has been reported [and they are commercially available], as has been reported there use in the preparation of oligomers. (See, e.g., Iribarren, et al. (1990) *Proc. Natl. Acad. Sci. (USA)* 87:7747–51; and Lesnik et al. (1983), *Biochemistry* 32:7832–8). The nucleosides are used to prepare dimer and trimer synthons using procedures described hereinabove. The synthon are used to prepare oligomers using methods such as those described in Examples 5, 6, 7, 9, 12, 13 or 15.

EXAMPLE 18

Preparation of a MP(Rp)/MP Dimer Synthon

A. Preparation of a (CT) Dimer Having a Chirally Pure Methylphosphonate Internucleosidyl Linkage Using Solution Phase Chemistry Into a 2 L roto-evaporator flask was placed 10.0 g (28 mM) of 3'-tert-butyldimethylsilyl thymidine and 26.1 g (35 mM) of 5'-dimethoxytrityl-N$^4$-isobutyryl-3'-methyl-N, N-diisopropylaminophosphoramidite-2'-deoxycytidine. The solids were dissolved in 500 ml of acetonitrile and evaporated to dryness under vacuum. This process was repeated with another 500 ml of acetonitrile and then the flask was released under argon and stoppered with a rubber septa.

This dry solid foam was then dissolved in 500 ml of acetonitrile ("ACN"), and with manual stirring, treated all at once with 404 ml tetrazole (180 mM, 0.45M tetrazole in THF). Manual stirring is continued for 30 seconds and then the flask is allowed to stand for another 2.5 minutes, after which time the reaction mix is treated all at once with 275 ml of an oxidizer solution (I$_2$/H$_2$O/lutidine/THF; 25 g/2.5 ml/100 ml/900 ml). The solution was stirred manually and allowed to stand at room temperature for 15 minutes. The resulting dark amber solution was then treated with bisulfite (2 g/25 ml/H$_2$O), which upon addition, turned the solution light amber as it reacted with the excess iodide. The reaction mix was then concentrated to a thick oil and taken up in ethyl acetate ("EtOAc") (500 ml) and washed with saturated sodium bicarbonate (2×250 ml) and H$_2$O(2×250 ml). The organic phase was dried over MgSO$_4$, filtered and concentrated to a light colored solid foam, which upon further drying yielded 35 grams of crude dimer.

The crude dimer was run on HPLC (reverse phase, Waters C18 bondapak) with a program (ACNMETH) starting with 50% acetonitrile and 0.1M triethylammonium acetate (TEAA, pH~7.0) which increased to 100% acetonitrile over 20 minutes with a linear gradient. Two major peaks were resolved, one at 4.5 minutes, which is residual lutidine and the other at 14.5 minutes which is the mixture of Rp and Sp diastereomers. The ratio of Rp and Sp was determined quantitatively by taking a 5 mg aliquot of the crude product and dissolving it in 1.5 ml of acetonitrile along with 0.5 ml of tetrabutylammonium fluoride (TBAF, 1M solution in THF). After standing at room temperature for 10 minutes the sample was run on HPLC. Two new peaks were observed at 6.5 and 7.1 minutes and the later eluting peak was gone. The first new peak, which is believed to be the Sp diastereomer, represented 66% (2/1) of the normalized value for the two peaks. The crude product was also analyzed by the (normal phase silica plate) in 75/25 EtOAc/CH$_2$Cl$_2$ ("75/25") with 5% methanol added. The tlc showed two spots with Rf's of 0.45 and 0.64, respectively; the faster running product (believed to be the Rp form) was less intense than the slower moving one.

The Rp diastereomer was separated on normal phase silica using a methanol step gradient in 75/25 EtOAc/CH$_2$Cl$_2$. A 7.5 cm by 60 cm column, was loaded with 700 g of silica (first slurried in 2.5 L of neat 75/25 EtOAc/CH$_2$Cl$_2$). The crude dimer was then dissolved in 75 ml of 75/25 EtOAc/CH$_2$Cl$_2$ and loaded onto the column. The column was started with 1% methanol and increased to 2% and finally 3% where the Rp dimer began to elute. The Rp dimer eluted cleanly over several bed volumes while maintaining 3% methanol in the eluent. The Sp dimer was eluted later with 30% methanol. The Rp dimer yield was 11.0 grams, while the Sp yield was 17.8 grams. HPLC analysis (ACNMETH) was performed on the Rp dimer and one peak was observed at 14.5 minutes. The tlc (75/25 EtOAc/CH$_2$Cl$_2$, 5% methanol) of this product, revealed a single spot product with an Rf of 0.55 which, upon treatment with 10% sulfuric acid in ethanol and heat, was both trityl and sugar positive.

The newly resolved Rp dimer, 11.0 g (0.011M) was dissolved in 110 ml of ACN and treated all at once at room temperature with 22 ml of TBAF (0.022M, 1M in THF). The reaction mix was allowed to stand overnight at ambient temperature. The next morning the reaction was determined to be complete by tlc (75/25 EtOAc/CH$_2$Cl$_2$ , 10% methanol); no starting material was detected but a small amount of 5'-DMT-dT was observed, which runs considerably faster on normal phase silica than the 3'-OH of the dimer. The reaction mixture was concentrated on a rotary evaporator to a thick oil which was then dissolved in CH$_2$Cl$_2$ (200 ml) and washed with saturated sodium bicarbonate (2×100 ml) and H$_2$O (2×100 ml). The organic phase was dried over MgSO$_4$ filtered, and concentrated to a light yellow solid foam, which was purified on 100 grams of silica (75/25, EtOAc/CH$_2$Cl$_2$ with 5% methanol). The 5'-DMT-dT was removed but an impurity at 13.5 minutes (HPLC, ACNMETH) was detected which was first believed to be unreacted starting material (t-BDMS on) but after additional treatment with TBAF this was found not to be the case. A second column, using 100 g of silica and the same eluent was run and smaller fractions were taken; the column was able to successfully separate the two spots. The pure CT-Rp dimer fractions were pooled and concentrated to yield 5.5 grams of a nearly white solid foam.

B. Preparation of a Chirally Pure Dimer Synthon

The CT-3'-OH dimer, 5.5 g (6 mM), prepared as described and hereinabove, was rendered anhydrous with two co-evaporations with pyridine. The resulting solid foam was released from the rotary evaporator with argon and stoppered with a rubber septa. The solid foam was dissolved in 100 ml of 9/1, ACN/CH$_2$Cl2, then treated with 1.7 ml triethylamine (TEA, 12 mM). With magnetic stirring, the reaction mix was treated dropwise at room temperature with 1.5 ml chloromethyl-N,N-diisopropylamino phosphine (Cl-MAP, 8 mM). The reaction was monitored on HPLC (ACNMETH) and after 1.5 hours was complete, showing two main products, one at 3.5 minutes which was pyridine and a second at 14.3 minutes which was the desired amidite.

The reaction mixture was concentrated on a rotary evaporator using a partial vacuum; the flask which contained the resulting light amber sludge was released under argon and capped. The crude product was immediately passed through a flash column containing 60 grams of silica (first equilibrated in 1/1/1 ACN/EtOAc/CH$_2$Cl$_2$ with 3% TEA). The product was eluted quickly with this eluent and all U.V. positive fractions were pooled and concentrated. The resulting solid foam was co-evaporated with ACN to remove any residual TEA, then dried overnight under full vacuum. The final product, an off white solid foam, weight 5.0 grams.

EXAMPLE 19

Preparation of MP(Rp)/MP(Rp)/DE Trimer Synthons

The above-identified trimer synthon is prepared using the dimer synthons of Example 18. The dimer synthon is coupled to a 5'-OH,3'-silylated nucleoside according to the methods of Example 18A for the coupling of the 3'-nucleoside to the monomer phosphoramidite.

The selected 5'-OH,3'-silylated nucleoside (1 equivalent) and isometrically pure Rp dimer methylphosphonamide (1.25 equivalents) are weighed into a round bottom flask and dried by co-evaporation with acetonitrile. The resulting foam is dissolved in acetonitrile and treated with a solution of 0.45M tetrazole in acetonitrile (4.5 equivalents). After 3 minutes, the reaction mixture is oxidized and the reaction product is worked up as described in Example 18A. The diastereoisomers of the 3'-silylated trimer are resolved on a silica gel column as described in Example 18A for resolution of the dimer isomers. The configuration of the diastereoisomers is determined using 2-D nmr (ROSEY). The trimer having the desired chiral configuration (Rp/Rp) of the two internucleosidyl linkages is converted to a trimer synthon by reaction with chloro-β-cyanoethoxy-N,N-diisopropylaminophosphoramidite using methods as described in Example 1B. The trimer synthon is worked up and purified using methods as described in Example 1B.

EXAMPLE 20

Preparation of an Oligomer Having MP(Rp)/MP/DE Internucleosidyl Linkages

The above-identified oligomer is prepared using the trimer synthons of Example 19 and by following the methods described in Example 8, substituting the trimer synthons for dimer synthons. All other parameters of synthesis, deprotection and purification are as described in Example 8.

EXAMPLE 21

Preparation of Oligoribonucleosides

Oligoribonucleotides may be synthesized using the following procedures:

The oligoribonucleotides were synthesized using 5'-O-dimethoxytrityl-2'-O-tert-butyldimethylsilyl-3'-O-N,N-diisopropyl-β-cyanoethylphosphoramidite nucleosides (Millipore, Hilford, Mass.). The syntheses were done on a 1 μmole scale with a Milligen 8750 automated DNA synthesizer using standard Milligen phosphoramidite procedures with the exception that the coupling times were extended to 12 minutes to allow adequate time for the more sterically hindered 2'-O-tert-butyldimethylsilyl RNA monomers to react. The syntheses were begun on control-pore glass bound 2'-O-tert-butyldimethylsilyl ribonucleosides purchased from Millipore. All other oligonucleotide synthesis reagents were as described in Millipore's standard protocols.

After synthesis, the oligonucleotides were handled under sterile, RNase-free conditions. Water was sterilized by overnight treatment with 0.5% diethylpyrocarbonate followed by autoclaving. All glassware was baked for at least 4 hours at 300° C.

The oligonucleotides were deprotected and cleaved from the support by first treating the support bound oligomer with 3/1 ammonium hydroxide/ethanol for 15 hours at 55° C. The supernatant, which contained the oligonucleotide, was then decanted and evaporated to dryness. The resultant residue was then treated with 0.6 mL of 1M tetrabutylammonium fluoride in tetrahydrofuran (which contained 5% or less water) for 24 hours at room temperature. The reaction was quenched by the addition of 0.6 mL of aqueous 2M triethylammonium acetate, pH 7. Desalting of the reaction mixture was accomplished by passing the solution through a Bio-Rad 10 DG column using sterile water. The desalted oligonucleotide was then dried.

Purification of the oligoribonucleotides was carried out by polyacrylamide gel electrophoresis (PAGE) containing 15% 19/1 polyacrylamide/bis-acrylamide and 7M urea using standard procedures (See Maniatis, T. et al., *Molecular Cloning: A Laboratory Manual*, pages 184–185 (Cold Spring Harbor 1982)). The gels were 20 cm wide by 40 cm long and 6 mm in width. The oligoribonucleotides (60 OD Units) were dissolved in 200 μL of water containing 1.25% bromophenol blue and loaded onto the gel. The gels were run overnight at 300 V. The product bands were visualized by UV backshadowing and excised, and the product eluted with 0.5M sodium acetate overnight. The product was desalted with a Waters C18 Sep-Pak cartridge using the manufacturer supplied protocol. The product was then $^{32}$P labelled by kinasing and analyzed by PAGE.

EXAMPLE 22

Preparation of Racemic Methylphosphonate Oligonucleotides

The oligomers were synthesized using 5'-(dimethoxytrityl) deoxynucleoside-3'-[(N,N-diisopropylamino)methyl]-phosphonoamidite monomers. Solid-phase synthesis was performed on methacrylate polymer supports with a Biosearch Model 8750 DNA synthesizer according to the manufacturer's recommendations except for the following modifications: the monomer, were dissolved in acetonitrile at a concentrations of 100 mM, except dG, which was dissolved in 1/1 acetonitrile/dichloromethane at 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A=10% acetic anhydride in acetonitrile. CAP B=0.625% N,N-dimethylaminopyridine in pyridine.

The dimethoxytrityl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/NH$_4$OH (9/9/1). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when combined with the supernatant. The combined solution was diluted to 30 ml total volume with water and neutralized with approximately 4 ml of 6N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column it was washed with 30 ml of water. The product was then eluted with 5 ml of 1/1 acetonitrile/water.

The oligonucleotide was purified by HPLC on a reverse phase column (Whatman RAC II) using a gradient of acetonitrile in 50 mM triethylammonium acetate.

EXAMPLE 23

Tm Studies of Oligomers Having an Alternating CT Sequence But Having Different Backbones A series of oligomers having the same nucleoside sequence (alternating CT) but having different backbones (different internucleosidyl linkages) were prepared as described in the examples herein. Chirally pure Rp dimers (CT) (prepared as described in Example 1A) were used to prepare the 2'-deoxy MP(Rp)/MP Oligomer. Rp(CU) dimers prepared according to Example 2 were used to prepare the 2'-O-Methyl-MP(Rp)/DE Oligomer. Control oligomers (a) 2'-deoxy all DE, having 2'-deoxy nucleosides and all phosphodiester internucleosidyl intakes and (b) 2'-O-methyl all DE, having 2'-O-methyl nucleosides and all phosphodiester internucleosidyl linkages were purchased from Oligos, Etc.

Hybridization experiments were conducted according to the following procedure:

Annealing reaction mixtures contained equimolar amounts of Oligomer and RNA target Oligomer (2.4 μM total strand concentration), 20 -mM potassium phosphate (pH 7.2), 100 mM sodium chloride, 0.1 mM EDTA and 0.03% potassium sarkosylate. The reaction mixtures were heated to 80° C. and then slowly cooled to 4° C. over about 4 to 6 hours. The annealed samples were then transferred to 1 cm quartz cuvettes and Tm was monitored by absorbance at 260 nm as a function of temperature using a Varian Cary Model 2E Spectrophotometer containing a temperature controlled 6×6 sample holder which interfaced with an IBM compatible PC computer. The temperature was varied from 5° C. to 80° C. at a ramp rate of 1° C./minute. The Tm for each melt profile is determined as the point corresponding to the maximum of the first derivative of the curve corresponding to absorbance versus temperature. Table II hereinbelow summarizes the results. These studies that these Oligomers having alternating MP Rp internucleosidyl linkages exhibit improved binding stability when hybridizing to an RNA target.

TABLE II

Tm's for Oligomers

| Sequence number | Backbone type | Tm |
|---|---|---|
| 2288-1 | Racemic all-methylphosphonate | 34.4°C. |
| 2286-1 | 2'-deoxy MP(Rp)/MP | 44.0°C. |
| — | 2'-O-methyl-MP(Rp)/MP | 47.4°C. |
| 2760-1 | 2'-deoxy MP(Rp)/DE | 53.8°C. |
| 2795-1 | 2'-deoxy all-DE | 60.80°C. |
| 2765-1 | 2'-O-methyl MP(Rp)/DE | 68.1°C. |
| 2792-1 | 2'-O-methyl all-DE | 75.0°C. |

EXAMPLE 24

Stability of Oligomers to 5'-Exonuclease Degradation by Snake Venom Phosphodiesterase The following example demonstrates (a) the enhanced nuclease stability of the 2'-deoxy MP(Rp)/DE backbone compared to an all-diester (DE) backbone; and (b) the enhanced nuclease stability of the 2'-O-methyl MP(Rp)/DE backbone compared to the 2'-deoxy MP(Rp)/DE backbone.

Oligomers were evaluated having the following sequence: 5'-CTCTCTCTCTCTCTA-3' (for 2'-deoxy sugars); or 5'-CUCUCUCUCUCUCUA-3' (for 2'-O-methyl sugars).

Snake venom phosphodiesterase I (PDE-I) from *crotalus adamanteus* was purchased from US Biochemicals, Inc. The all-diester (DE) backbone oligomer was purchased from Oligos Etc. The other oligomers were synthesized as described in the preceding examples.

Aliquots of each oligomer (0.075 $A_{260}$ units) were pipetted into polypropylene microcentrifuge tubes and dried in a Speed-Vac™ vacuum centrifuge (Savant, Inc.). Next, the tubes were placed on ice and aliquots of PDE-I were added to each tube (0.19 unit in 95 µl of 10 mM Tris-HCl, pH 8.8, 2 mM $MgCl_2$ 0.4% glycerol). The zero time point samples were diluted immediately with acetonitrile (35 µl), frozen in a dry ice/isopropanol bath, and stored at −20° C. for analysis at a later time. The remaining samples were then placed in a water bath at 37° C. Samples for each specified time point were then removed form the water bath, diluted with acetonitrile and frozen as described for the zero time point samples.

At the conclusion of the nuclease degradation experiment, the samples were individually thawed and analyzed immediately be reversed phase HPLC using a Beckman System Gold apparatus with a Model 126 binary gradient pump module and a Model 168 Diode Array Detector. The samples were injected onto the column using a manual injector with a 2000 µl sample loop. A Vydac C4 Protein column was used for these experiments (Vydac cat. No. 901019, 4.6 mm i.d.×250 mm long). Elution was done with a dual solvent system: Buffer A=1% acetonitrile in 50 mM triethyl ammonium acetate (TEAA, pH 7.0); Buffer B=50% acetonitrile in 50 mM TEAA (pH 7.0). Solvent flow rates were increased from 0.05 to 1.0 ml/minutes over the first minute of the run and then held at 1.0 ml/minute for the remainder of the run. Gradient conditions for each backbone were as follows: All-DE backbone-5–25% Buffer B (2.5–9 minute), 25–45% Buffer B (9.0–22.5 minute) 45–100% Buffer B (22.5–28.0 minute); 2'-deoxy MP(Rp)/DE backbone- 5–35% Buffer B (2.5–12.5 minute), 35–50% Buffer B (12.5–22.5 minute), 50–100% Buffer B (22.5–27.5 minute); 2'-O-methyl MP(Rp)/DE backbone- 5–50% Buffer B (2.5–17.5 minute), 50–65% Buffer B (17.5–27.5 minute), 65–100% Buffer B (27.5–31.0 minute). Average retention times for each backbone oligomer (undegraded) were as follows:

| All-DE | 15.7 minutes |
|---|---|
| 2'-deoxy Mp(Rp)/DE | 18.5 minutes |
| 2'-O-methyl Mp(Rp)/DE | 18.6 minutes |

Degradation was determined by the appearance of earlier eluting peaks and a decrease in area (or complete loss) of the peak corresponding to the full-length oligomer. Percent degradation was determined by comparing the peak heights and peak areas for each time point at 37° C. to the zero time point. The half-lives for each oligomer in the presence of PDE-I were then determined by plotting log (% full-length) versus time and finding the value corresponding to log (50%)=1.699. The following results were obtained from two separate experiments.

TABLE III

| Oligomer | $T_{1/2}$ |
|---|---|
| (a) Comparison of All-DE backbone oligomer to 2'-deoxy-MP(Rp)/DE backbone oligomer. | |
| All-DE | <1 minute |
| 2'-deoxy MP(Rp)/DE | 12.5 minutes |
| (b) Comparison of 2'-deoxy MP(Rp)/DE backbone oligomer to 2'-O-methyl MP(Rp)/DE backbone oligomer. | |
| 2'-deoxy MP(Rp)/DE | 10 minutes |
| 2'-O-methyl MP(Rp)/DE | 350 minutes |

EXAMPLE 25

Stability of 2'-deoxy MP(Rp)/DE Oligomer in Cytoplasmic Lysate From HeLa Cells

This example demonstrates that the 2'-deoxy mixed backbone oligomer is completely stable in HeLa cell lysate within the limits of detection over the time course of the experiment.

HeLa cell cytoplasmic lysate was purchased from Endotronics, Inc. (Minneapolis, Minn.). This preparation is a hypotonic dounce lysis in 5× the packed cell volume. It was buffered to pH 6.0 by adding 0.4 ml of 2-(N-morpholino) ethanesulfonate (MES, 0.5M solution, pH 6.0) to 3.6 ml of cell lysate on ice and mixing with mild agitation.

Aliquots of oligomer were dried and then diluted with HeLa cell lysate (95 µl) as described in the preceding example. Samples were then incubated at 37° C. and analyzed as described in Example 24.

TABLE IV

| Oligomer | $T_{1/2}$ |
|---|---|
| All-DE | 1.4 hours |
| 2'-deoxy MP(Rp)/DE | No degradation observed over 72 hours incubation at 37° C. |

EXAMPLE 26

Stability of 2'-deoxy MP(Rp)/DE and 2'-O-methyl MP(Rp)/DE Backbone Oligomers in Cytoplasmic Lysate From African Green Kidney COS-7 Cells The following example demonstrates that a 2'-deoxy MP(Rp)/DE and 2'-O-methyl MP(Rp)/DE backbone oligomers are at least 500 times more stable to degradation in COS-7 cell lysate then the corresponding All-DE backbone oligomers having the same sequence.

COS-7 cell lysate for these experiments was prepared as follows. COS-7 cells were grown to 90% confluency and then harvested in the presence of 0.25% trypsin. The cell pellets were swashed twice with phosphate buffered saline and then frozen overnight at −20° C. Next, the pellets were resuspended in approximately an equal volume of lysis buffer (2.5 mM HEPES, pH 7.2, 2.0 mM $MgCl_2$, 0.1% NP-40), drawn up and down ten times through a sterile 1 ml polypropylene pipette, and then centrifuged at 10,000×G for 5 minutes. Approximately 40% of the resulting supernatant was then used to lyse the cell pellet in a dounce homogenizer (Type A pestle) with twenty strokes. This suspension was then centrifuged as above and the supernatant was combined with the rest of the supernatant from the first resuspension. The resulting solution represents predominantly cytosolic lysate without any nuclear debris and is approximately 1–1.5 times the volume of the original packed cell pellet. Aliquots from the resulting cell lysate were buffered with either 25 mM Tris-acetate (final pH 7.4) or 25 mM MES (final pH 6.0) prior to incubation with oligomer.

Aliquots of each oligomer (0.075) $A_{260}$ unit) were dried in sterile polypropylene microcentrifuge tubes and then resuspended in 10 µl of COS-7 cell lysate on ice. Water (90 µl) and acetonitrile (35 µl) were added immediately to the zero time samples and they were frozen in a dry ice/ethanol bath and stored at −20° C. for later analysis. The remaining samples were then incubated in a water bath at 37° C. At specified time points, samples were removed from the water bath, diluted with water and acetonitrile and frozen exactly as described for the zero time point controls.

Following the incubations with cell lysate, the samples were individually thawed, diluted with water (535 µl) and analyzed immediately by reversed phase HPLC as described in Example 24. Degradation was determined from the resulting chromatograms as described in Example 26. The results are summarized in Table V below:

TABLE V

| Oligomer | $T_{1/2}$ |
| --- | --- |
| All-DE backbone oligomer | <5 minutes. No full length oligomer remained after 5 minutes of incubation at 37° C. |
| 2'-O-methyl all-DE backbone | ~5 hours. |
| 2'-deoxy MP(Rp)/DE backbone | ~35 hours. (Approximately 35% loss of peak corresponding to full-length oligomer after 24 hours incubation at 37° C.) |
| 2'-O-methyl MP(Rp)/DE | 100% stable over a 24 hour incubation at 37° C. |

EXAMPLE 27

Stability of 2'-deoxy MP(Rp)/DE Backbone Oligomer in Bacterial Cell Lysate From *Escheria coli*

The following example demonstrates that a 2'-deoxy MP(Rp)/DE oligomer is at least 2,000 fold more stable than an all-DE oligomer having the same sequence in cell lysate from *E. coli*.

*E. coli* cell lysate was prepared as follows. Approximately 2×1011 cells were pelleted by centrifugation, resuspended in 10 ml of Tris-HCl (50 mM, pH 7.5) and incubated at room temperature for five minutes. Next, dithiothreitol and lysozyme were added to final concentrations of 2 mM and 1 mg/ml, respectively, and the resulting suspension was incubated at 37° C. for 30 minutes. The mixture was then sonicated briefly ten times on ice and centrifuged at 7,000 rpm for 20 minute. Based on visual inspection, it was estimated that this procedure had not sufficiently lysed the cells, so the supernatant (vol.=5 ml) was collected and stored at 4° C. and the cell pellet was resuspended in 1 ml of Tris-HCl (50 mM, pH 7.5). The resuspended cell pellet was exposed to five rounds of freeze/thaw, sonicated briefly to break up the chromosomal DNA, and then centrifuged at 8,000 rmp for 5 minutes. The resulting supernatant (approx. 70 µl) was then combined with the supernatant from the previous step (approx. 5 ml) and centrifuged at 6,000×G for 5 minutes to pellet any residual debris. The final supernatant was estimated to contain approximately 50% lysed cells in approximately 57 times the original cell pellet volume (100 µl).

Aliquots of the oligomers (0.050 $A_{260}$ units) were dried in sterile polypropylene microcentrifuge tubes and resuspended in 95 µl of cell lysate on ice. Incubations at 37° C., HPLC analysis, and quantitation of oligomer degradation were done exactly as described in Example 24. The results are summarized below:

TABLE VI

| Oligomer | $T_{1/2}$ |
| --- | --- |
| All-DE | 1–3 minutes. |
| 2'-deoxy MP(Rp)/DE | ~65 hours. (84.5% full-length oligomer remained after 20.5 hours incubation at 37° C.) |

EXAMPLE 28

Stability of 21-deoxy MP(Rp)/DE Backbone Oligomer in Bacterial Cell Lysate from *Staphylococcal aureus*

The following example demonstrates that a 2'-deoxy MP(Rp)/DE oligomer is at least 400 fold more stable than an all-DE oligomer having the same sequence in cell lysate from *S. aureus*.

*S. aureus* cell lysate was prepared at described for *E. coli* in Example #4 except with the following modifications: (i) the lysis was conducted with a cell pellet containing approximately 4×1010 cells; (ii) lysostaphin was used instead of lysozyme (500 units, Sigma, Inc.); and (iii) a total of 10 freeze/thaw cycles were used instead of 5.

Incubation with oligomers at 37° C., HPLC analysis and determination of oligomer degradation from the chromatograms were conducted exactly as described for the experiment with *E. coli* in Example 27. The results are summarized below:

TABLE VII

| Oligomer | $T_{1/2}$ |
|---|---|
| All-DE | 13 minutes |
| 2'-deoxy MP(Rp)/DE | ~75 hours. (86.4% full-length oligomer remained after 20.5 hours incubation at 37° C.) |

We claim:

1. A method of making a synthetic Oligomer which hybridizes to an RNA target sequence, said method comprising the steps of:

(a) identifying a single stranded RNA target sequence.

(b) synthesizing a nucleoside dimer, trimer or tetramer having racemic internucleosidyl phosphonate linkages;

(c) purifying from said racemic nucleoside dimer, trimer or tetramer a chirally pure nucleoside dimer, trimer or tetramer; and (d) sequentially linking two or more of said chirally pure nucleoside dimers, trimers or tetramers to form a synthetic oligomer having chirally pure phosphonate internucleosidyl linkages selected from the group consisting of lower alkylphosphonate internucleosidyl linkages of 1 to 3 carbon atoms and lower alkylphosphonate internucleosidyl linkages of 1 to 3 carbon atoms which are mixed with non-phosphonate internucleosidyl linkages wherein the chirally pure phosphonate linkages are interspersed between single non-phosphonate internucleosidyl linkages in a ratio of from 1 non-phosphonate linkage to about 1 phosphonate linkage to 1 non-phosphonate linkage to about 4 phosphonate linkages, and wherein the Oligomer is substantially complementary to said identified RNA target sequence.

2. A method according to claim 1 wherein said chirally pure phosphonate linkages are Rp lower alkylphosphonate linkages of 1 to 3 carbon atoms.

3. A method according to claim 2 wherein said Rp lower alkylphosphonate linkages are Rp methylphosphonate linkages.

4. A method according to claim 3 wherein said ratio of non-phosphonate linkages to phosphonate linkages is from about 1 to 1 to about 1 to 2.

5. A method according to claim 3 wherein the nucleosides of said oligomer have 2'-substituted ribosyl groups as sugar moieties selected from the group consisting of 2'-O-alkylribosyl of 1 to 10 carbon atoms, 2'-halo-ribosyl, 2'-O-alkenyl ribosyl of 3 to 6 carbon atoms and 2'-deoxyribosyl.

6. A method according to claim 1 wherein said non-phosphonate linkages are selected from the group consisting of phosphodiester, phosphotriester, phosphorothioate, phosphorodithioate, phosphoramidate, phosphorofluoridate, boranophosphate, formacetal and silyl.

7. A method according to claim 1 wherein said Oligomer is synthesized by linking together chirally pure nucleoside dimers of the formula:

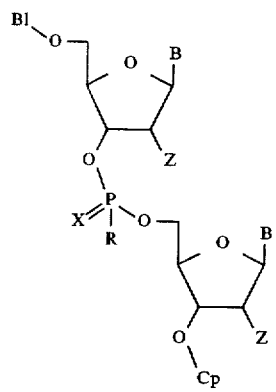

wherein X is oxygen or sulfur, R is alkyl of from 1 to 3 carbon atoms; Z is hydrogen, alkoxy of from 1 to 10 carbon atoms, halogen or alkenyloxy of 3 to 6 carbon atoms; B is an optionally protected purine or pyrimidine base; Bl is a blocking group and Cp is a coupling group.

8. A method according to claim 7 wherein X is oxygen and R is methyl.

9. A method according to claim 8 wherein the chirally pure phosphonate linkages are Rp.

10. A method according to claim 9 wherein Z is hydrogen or methoxy.

11. A method according to claim 10 wherein the non-phosphonate linkages are phosphodiester linkages.

12. A method according to claim 11 wherein Z is methoxy.

13. A synthetic Oligomer having activity in preventing or interfering with expression or translation of a single stranded RNA target sequence wherein said synthetic Oligomer is a Oligomer having chirally sure phosphonate internucleosidyl linkages selected from the group consisting of lower alkylphosphonate internucleosidyl linkages of 1 to 3 carbon atoms which are mixed with non-phosphonate internucleosidyl linkages wherein the phosphonate linkages are interspersed between single non-phosphonate linkages in a ratio of from about 1 to 1 to about 1 to 4 non-phosphonate linkages to phosphonate linkages and wherein Oligomer is substantially complementary to the RNA target sequence wherein at most three out of every four adjacent linkages can have a preselected chirality.

14. An oligomer according to claim 13 wherein said phosphonate linkages are chirally pure Rp methylphosphonate linkages.

15. An oligomer according to claim 14 wherein said non-phosphonate linkages are selected from the group consisting of phosphodiester, phosphotriester, phosphorothioate, phosphorodithioate, phosphoramidate, phosphorofluoridate, boranophosphate, formacetal and silyl.

16. An oligomer according to claim 15 wherein the nucleosides of said oligomer have 2'-O-methyl ribosyl groups as sugar moieties.

17. A synthetic oligomer preparation consisting of oligomers having chirally pure phosphonate internucleosidyl linkages selected from the group consisting of lower alkyl phosphonate linkages of 1 to 3 carbon atoms and lower alkylphosphonothioate linkages of 1 to 3 carbon atoms mixed with non-phosphonate linkages, wherein the oligomers have phosphonate linkages interspersed between single non-phosphonate linkages, wherein the oligomers are complementary to a RNA target sequence, and wherein the oligomer preparation demonstrates enhanced "net" binding affinity for the complementary RNA target sequence wherein at most three out of every four adjacent linkages can have a preselected chirality.

18. A method for preparing an oligomer having a predetermined base sequence of nucleoside units and having chirally pure phosphonate internucleosidyl linkages mixed with non-phosphonate internucleosidyl linkages wherein the phosphonate internucleosidyl linkages are interspersed between single non-phosphonate internucleosidyl linkages, which method comprises linking together individual nucleoside dimers, trimers or tetramers having chirally pure phosphonate internucleosidyl linkages wherein at most three out of every four adjacent linkages can have a preselected chirality.

19. A method according to claim 1 wherein said oligomer is synthesized by linking together chirally pure synthons of the formula:

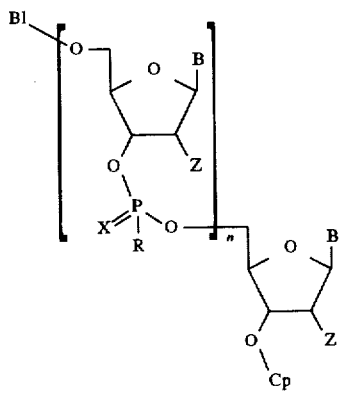

wherein X is oxygen or sulfur, R is alkyl of 1 to 3 carbon atoms; Z is hydrogen alkoxy of 1 to 10 carbon atoms, halogen or alkenyloxy of 3 to 6 carbon atoms; B is an optionally protected purine or pyrimidine base; Bl is a blocking group; n is 1, 2 or 3 and Cp is a coupling group.

20. A chirally pure synthon of the formula:

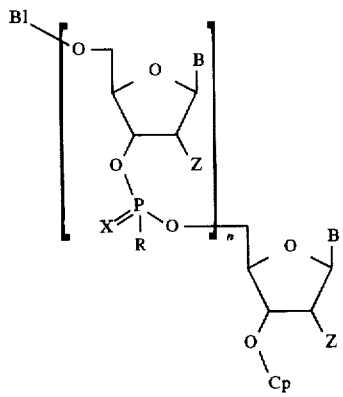

wherein X is oxygen or sulfur, R is alkyl of 1 to 3 carbon atoms; Z is hydrogen alkoxy of 1 to 10 carbon atoms, halogen or alkenyloxy of 3 to 6 carbon atoms; B is an optionally protected purine or pyrimidine base; Bl is a blocking group; n is 1, 2 or 3 and Cp is a coupling group.

* * * * *